United States Patent
Grassian et al.

(10) Patent No.: US 11,952,572 B2
(45) Date of Patent: Apr. 9, 2024

(54) METHODS OF TREATING CANCER BY INHIBITING SETD2

(71) Applicant: EPIZYME, INC., Cambridge, MA (US)

(72) Inventors: Alexandra Rose Grassian, Cambridge, MA (US); Michael Thomenius, Arlington, MA (US); Jennifer Anne Totman, Berlin, MA (US)

(73) Assignee: Epizyme, Inc., Cambridge, MA (US)

( * ) Notice: Subject to any disclaimer, the term of this patent is extended or adjusted under 35 U.S.C. 154(b) by 481 days.

(21) Appl. No.: 16/639,424

(22) PCT Filed: Aug. 14, 2018

(86) PCT No.: PCT/US2018/046698
§ 371 (c)(1),
(2) Date: Feb. 14, 2020

(87) PCT Pub. No.: WO2019/036466
PCT Pub. Date: Feb. 21, 2019

(65) Prior Publication Data
US 2021/0002645 A1 Jan. 7, 2021

Related U.S. Application Data

(60) Provisional application No. 62/545,353, filed on Aug. 14, 2017.

(51) Int. Cl.

| | |
|---|---|
| *A61K 31/7076* | (2006.01) |
| *A61K 31/7088* | (2006.01) |
| *A61K 38/46* | (2006.01) |
| *A61K 39/395* | (2006.01) |
| *A61P 35/00* | (2006.01) |
| *C07K 16/40* | (2006.01) |
| *C12N 5/00* | (2006.01) |
| *C12N 5/09* | (2010.01) |
| *C12N 9/22* | (2006.01) |
| *C12N 15/11* | (2006.01) |
| *C12N 15/113* | (2010.01) |

(52) U.S. Cl.
CPC ...... *C12N 15/1137* (2013.01); *A61K 31/7076* (2013.01); *A61K 31/7088* (2013.01); *A61K 38/465* (2013.01); *A61K 39/3955* (2013.01); *A61P 35/00* (2018.01); *C07K 16/40* (2013.01); *C12N 5/0693* (2013.01); *C12N 9/22* (2013.01); *C12N 15/11* (2013.01); *C07K 2317/76* (2013.01); *C12N 2310/14* (2013.01); *C12N 2310/20* (2017.05); *C12N 2800/80* (2013.01)

(58) Field of Classification Search
CPC .... A61P 35/02; A61K 31/7076; C12N 5/0693
See application file for complete search history.

(56) References Cited

U.S. PATENT DOCUMENTS

| | | | |
|---|---|---|---|
| 4,582,788 A | 4/1986 | Erlich | |
| 4,595,766 A | 6/1986 | Roloff et al. | |
| 4,683,194 A | 7/1987 | Saiki et al. | |
| 4,683,202 A | 7/1987 | Mullis | |
| 2009/0082560 A1 | 3/2009 | Kobayashi et al. | |
| 2011/0021362 A1 | 1/2011 | Trojer et al. | |
| 2011/0136807 A1 | 6/2011 | Hangauer, Jr. | |
| 2013/0137748 A1 | 5/2013 | Hamamoto et al. | |
| 2014/0303106 A1* | 10/2014 | Zheng ............... | C07D 473/34 536/27.3 |
| 2017/0044100 A1 | 2/2017 | Bishai et al. | |
| 2017/0355695 A1 | 12/2017 | Foley et al. | |
| 2021/0002645 A1 | 1/2021 | Grassian et al. | |
| 2023/0049113 A1 | 2/2023 | Thomenius et al. | |
| 2023/0075198 A1 | 3/2023 | Lampe et al. | |
| 2023/0133671 A1 | 5/2023 | Raimondi et al. | |

FOREIGN PATENT DOCUMENTS

| | | |
|---|---|---|
| CN | 106317043 A | 1/2017 |
| EP | 0050424 A1 | 4/1982 |
| EP | 0084796 A2 | 8/1983 |
| EP | 0201184 A2 | 11/1986 |
| EP | 0237362 A1 | 9/1987 |
| EP | 0258017 A1 | 3/1988 |
| EP | 1880994 A1 | 1/2008 |
| EP | 1942105 A1 | 7/2008 |
| JP | 2012-107001 A | 6/2012 |
| WO | 2002080926 A1 | 10/2002 |
| WO | 2004018428 A1 | 3/2004 |
| WO | 2004018461 A2 | 3/2004 |
| WO | 2009158375 A1 | 12/2009 |
| WO | 2010028192 A1 | 3/2010 |
| WO | 2011079102 A1 | 6/2011 |

(Continued)

OTHER PUBLICATIONS

Li et al., 2016, Oncotarget. 7(31): 50719-50733.*
Zips et al., 2005. in vivo, 19: 1-8.*
Altschul et al., "Local alignment statistics," Methods in Enzymology 266:460-480, Elsevier, Netherlands (1996).
Altschul et al., "Gapped BLAST and PSI-BLAST: a new generation of protein database search programs," Nucleic Acids Res. 25:3389-3402, Oxford Press, England (1997).

(Continued)

*Primary Examiner* — Zachary C Howard
(74) *Attorney, Agent, or Firm* — Dechert LLP; Andrea L. C. Reid; Danielle M. Paglia

(57) ABSTRACT

The present disclosure provides methods and pharmaceutical compositions for treating or slowing the progression of cancer, i.e., pancreatic cancer or esophageal cancer, by administering to a human subject in need thereof a therapeutically effective amount of an inhibitor of the histone methyltransferase, SETD2.

1 Claim, 7 Drawing Sheets

Specification includes a Sequence Listing.

(56) References Cited

FOREIGN PATENT DOCUMENTS

| WO | 2015143424 A2 | 9/2015 |
| WO | 2015150097 A1 | 10/2015 |
| WO | 2015164482 A1 | 10/2015 |
| WO | 2016010950 A1 | 1/2016 |
| WO | 2016040505 A1 | 3/2016 |
| WO | WO 2016/079321 A1 | 5/2016 |
| WO | WO 2017/106259 A1 | 6/2017 |
| WO | 2019036466 A1 | 2/2019 |
| WO | WO 2020037079 A1 | 2/2020 |
| WO | WO 2020112872 A1 | 6/2020 |
| WO | 2021168313 A1 | 8/2021 |
| WO | 2022261243 A1 | 12/2022 |
| WO | 2023077117 A1 | 5/2023 |

OTHER PUBLICATIONS

Chen, S. et al., "CRISPR-Cas9: from Genome Editing to Cancer Research," Int. J Biol. Sci. 12: 1427-1436 (2016).

Edmunds, J.W. et al., "Dynamic histone H3 methylation during gene induction: HYPB/Setd2 mediates all H3K36 trimethylation," The EMBO Journal 27:406-420, EMBO Press, Germany (2008).

Fonfara, I et al., "The CRISPR-associated DNA-cleaving enzyme Cpf1 also processes precursor CRISPR RNA," Nature 532: 517-521, Nature Publishing, England (2016).

Fontebasso, AM. et al., "Mutations in SETD2 and genes affecting histone H3K36 methylation target hemispheric high-grade gliomas," Acta Neuropathol. 125: 659-669, Springer Publishing, United States (2013).

Gaj, T. et al., "ZFN, TALEN, and CRISPR/Cas-based methods for genome engineering," Trends Biotechnol 31:397-405, Elsevier, Netherlands (2013).

Johnson et al, "End points and United States Food and Drug Administration approval of oncology drugs," J Clin. Oncol. 21:1404-1411 (2003).

Karlin et al., "Methods for assessing the statistical significance of molecular sequence features by using general scoring schemes," Proc. Natl. Acad Sci. 87:2264-2268, National Academy of Science, United States (1990).

Karlin et al., "Applications and statistics for multiple high-scoring segments in molecular sequences" Proc. Natl. Acad Sci. 90:5873-5877 (1993).

Larkin, J., et al., "Epigenetic regulation in RCC: opportunities for therapeutic intervention?" Nature Reviews 9: 147-155 (2012).

Li, J. et al., "SETD2: an epigenetic modifier with tumor suppressor functionality," Oncotarget 7:50719-50734, Impact Journals, United States (2016).

Maeder, M.L. and Gersbach, C.A., "Genome-editing Technologies for Gene and Cell Therapy," Mol. Ther. 24: 430-446, Elsevier, Netherlands (2016).

Myers and Miller, "Optimal alignments in linear space," CABIOS 4:11-17, Oxford Press, England (1988).

Needleman and Wunsch, "A General Method Applicable to the Search for Similiarities in the Amino Acid Sequence of Two Proteins," J Mol. Biol. 48:443-453, Elsevier, Netherlands (1970).

Newbold, R.F. and Mokbel, K., "Evidence for a tumour suppressor function of SETD2 in human breast cancer: a new hypothesis," Anticancer Research 30: 3309-3311, International Institute of Anticancer Research (2010).

Perez-Pinera, P. et al., "Advances in targeted genome editing," Curr Opin Chem Biol 16:268-277, Elsevier, Netherlands (2012).

Sanchez-Rivera, F.J. and Jacks, T., "Applications of the CRISPR-Cas9 System in Cancer Biology," Nat Rev Cancer 15: 387-395, Nature Publishing England (2015).

Smith and Waterman, "Comparison of biosequences," Advances in Applied Mathematics 2: 482-489, Academic Press, United States (1981).

Zetsche, B. et al., "Cpf1 Is a Single RNA-Guided Endonuclease of a Class 2 CRISPR-Cas System," Cell 163:759-771, Elsevier, Netherlands (2015).

Zheng, W. et al., "Sinefungin derivatives as inhibitors and structure probes of protein lysine methyltransferase SETD2," J Am. Chem. Soc. 134: 18004-18014, American Chemical Society (2012).

Zhu, X. et al., "Identification of functional cooperative mutations of SETD2 in human acute leukemia," Nature Genetics 46: 287-293, Nature Publishing, England (2014).

International Search Report and Written Opinion for International Application No. PCT/US2018/046698, European Patent Office, Netherlands, dated Oct. 19, 2018, 8 pages.

Bingham et al., "Over one hundred solvates of sulfathiazole," Chemical Communications. 2001;7(7):603-604.

Caira et al., "Preparation and crystal characterization of a polymorph, a monohydrate, and an ethyl acetate solvate of the antifungal fluconazole," 2003;93(3):601-11.

Chang et al., "Investigation of the inhibitors of histone-lysine N-methyltransferase SETD2 for acute lymphoblastic leukaemia from traditional Chinese medicine," SAR QSAR Environ Res. 2016;27(7):589-608.

Chavda et al., "A novel achiral seco-cyclopropylpyrido[e]indolone (CPyI) analog of CC-1065 and the duocarmycins: synthesis, DNA interactions, in vivo anticancer and anti-parasitic evaluation," Bioorg Med Chem. 2010;18(14):5016-24.

Chen et al., "Histone methyltransferase SETD2: a potential tumor suppressor in solid cancers," J Cancer. 2020; 1(11):3349-3356.

Chesi et al., "The t(4;14) Translocation in Myeloma Dysregulates Both FGFR3 and a Novel Gene, MMSET, Resulting in IgH/MMSET Hybrid Transcripts," Blood. 1998;92(9):3025-34.

"CID 108791761 Compound Summary: 7-Chloro-N-pyridin-2-yl-1H-indole-2-carboxamide," PubChem. Created Jan. 15, 2016: https://pubchem.ncbi.nlm.nih.gov/compound/108791761.

"CID 110853847 Compound Summary: ethyl 4-[(7-methyl-1H-indole-2-carbonyl)amino]piperidine-1-carboxylate," PubChem. Created Jan. 18, 2016: https://pubchem.ncbi.nlm.nih.gov/compound/110853847.

"CID 131900417 Compound Summary: (6-Methoxy-3,4-dihydro-1H-isoquinolin-2-yl)-(3,4,7-trimethyl-1H-indol-2-yl) methanone," PubChem. Created Dec. 12, 2017: https://pubchem.ncbi.nlm.nih.gov/compound/131900417.

Daigle et al., "Selective Killing of Mixed Lineage Leukemia Cells by a Potent Small-Molecule DOT1L Inhibitor" Cancer Cell. 2011;20:53-65.

Engelhardt et al., "Detailed structure-activity relationship of indolecarboxamides as H4 receptor ligands," Eur J Med Chem. 2012;54:660-8.

Fahey and Davis, "SETting the Stage for Cancer Development: SETD2 and the Consequences of Lost Methylation," Cold Spring Harb Perspect Med. May 1, 2017;7(5):a026468.

Goossens et al., "Cancer biomarker discovery and validation," Transl Cancer Res. 2015;4(3):256-269.

Gupta and Zhang, "Angiogenesis: a curse or cure?," Postgrad Med J. 2005;81:236-242.

Hadjipavlou-Litina et al., "2D-QSAR and 3D-QSAR/CoMFA analyses of the N-terminal substituted anthranilic acid based CCK(1) receptor antagonists: 'Hic Rhodus, hic saltus'," Bioorg Med Chem. 2009;17(14):5198-206.

Herzog et al., "Trabectedin Followed by Irinotecan Can Stabilize Disease in Advanced Translocation-Positive Sarcomas with Acceptable Toxicity," 2016;2016:7461783.

Hudlebusch et al., "The Histone Methyltransferase and Putative Oncoprotein MMSET Is Overexpressed in a Large Variety of Human Tumors," Clin Cancer Res. 2011;17(9):2919-29.

Jin and Zhou, "Crucial role of the pentose phosphate pathway in malignant tumors," Oncology Letters. 2019;17(5):4213-4221.

Kalff and Spencer, "The t(4;14) translocation and FGFR3 overexpression in multiple myeloma: prognostic implications and current clinical strategies," Blood Cancer Journal. 2012;2:89.

Kamel et al., "Exploitation of Gene Expression and Cancer Biomarkers in Paving the Path to Era of Personalized Medicine," Genomics Proteomics Bioinformatics. 2017;15(4):220-235.

Kassambara, et al., "MMSET is overexpressed in cancers: link with tumor aggressiveness," Biochemical and Biophysical Research Communications. 2009;379(4):840-845.

(56) References Cited

OTHER PUBLICATIONS

Konikova and Kusenda, "Altered expression of p53 and MDM2 proteins in hematological malignancies," Neoplasma. 2003;50(1):31-40.

Kuo et al., "NSD2 links dimethylation of histone H3 at lysine 36 to oncogenic programming," Molecular Cell. 2011;44:609-20.

Kwak et al. "Structure-activity relationship of indoline-2-carboxylic acid N-(substituted)phenylamide derivatives," Bioorg Med Chem Lett. Aug. 1, 2010;20(15):4620-3.

Morera et al., "Targeting histone methyltransferases and demethylases in clinical trials for cancer therapy," Clinical Epigenetics. 2016;8(57):1-16.

Mullis et al., "Specific enzymatic amplification of DNA in vitro: the polymerase chain reaction," Cold Spring Harb Symp Quant Biol. 1986;51 Pt 1:263-73.

NCBI GenBank, "*Homo sapiens* SET domain containing 2, histone lysine methyltransferase (SETD2), transcript variant 1, mRNA," ncbi.nlm.nih.gov, Accession No. NM_014159.6, accessed at URL:[https://www.ncbi.nlm.nih.gov/nuccore/NM_014159.6] on Dec. 23, 2021, 12 pages.

NCBI Gene, "SETD2 SET domain containing 2, histone lysine methyltransferase [ *Homo sapiens* (human) ]," ncbi.nlm.nih.gov, Gene ID: 29072, HGNC: 18420, accessed at URL:[https://www.ncbi.nlm.nih.gov/gene?Db=gene&Cmd=DetailsSearch&Term=29072] on Dec. 23, 2021, 12 pages (Dec. 2021).

Ohri et al., "Tumour necrosis factor-alpha expression in tumour islets confers a survival advantage in non-small cell lung cancer," BMC Cancer. 2010;10:323.

Park et al., "Metabolism of fluorine-containing drugs," Annu Rev Pharmacol Toxicol. 2001;41:443-70.

Park et al.,"Methylation of Aurora kinase A by MMSET reduces p53 stability and regulates cell proliferation and apoptosis," Oncogne. 2018;37:6212-24.

Pawlyn and Morgan, "Evolutionary biology of high-risk multiple myeloma," Nature Reviews. Cancer. 2017;17(9):543-56.

PCT International Search Report and Written Opinion from PCT/US2019/046569, dated Nov. 5, 2019.

PCT International Search Report and Written Opinion from PCT/US2019/063405, dated Apr. 21, 2021.

PCT International Search Report and Written Opinion from PCT/US2021/018863, dated Jul. 20, 2021.

PCT International Search Report and Written Opinion from PCT/US2022/032718, dated Sep. 12, 2022.

PCT International Search Report and Written Opinion from PCT/US2022/078962, dated Jan. 26, 2023.

Prideaux et al., "The genetic architecture of multiple myeloma," Advances in Hematology. 2014:1-16.

Slagle et al., "Expression of ras, c-myc, and p53 proteins in cervical intraepithelial neoplasia," Cancer. 1998;83(7):1401-8.

Thomenius, et al., "Identification of a First-in-Class SETD2 Inhibitor That Shows Potent and Selective Anti-Proliferative Activity in t(4;14) Multiple Myeloma: T(4;14) Multiple Myeloma Cells Are Dependent on Both H3K36 Di and Tri-Methylation," Blood. 2018;132(Supplement1):3207.

Tisi et al., "Structure of the Epigenetic Oncogene MMSET and Inhibition by N-Alkyl Sinefungin Derivatives," ACS Biol. 2016;11(11):3093-3105.

Van Tonder et al., "Preparation and physicochemical characterization of 5 niclosamide solvates and 1 hemisolvate," AAPS PharmSciTech. 2004;5(1):E12.

Xie et al., "MMSET regulates expression of IRF4 in t(4;14) myeloma and its silencing potentiates the effect of bortezomib," Leukemia. 2015;29:2347-54.

Maeda and Khatami, "Analyses of repeated failures in cancer therapy for solid tumors: poor tumor-selective drug delivery, low therapeutic efficacy and unsustainable costs," Clin Trans Med. 2018;7:11.

Gura, "Systems for Identifying New Drugs are Often Faulty," Science. 1997;278, 1041-1042.

Johnson et al., "Relationships between drug activity in NCI preclinical in vitro and in vivo models and early clinical trials," British Journal of Cancer. 2001;84(10):1424-1431.

Shi et al., "Discovery of cancer drug targets by CRISPR-Cas9 screening of protein domains," Nat Biotechnol. 2015;33 (6):661-7.

\* cited by examiner

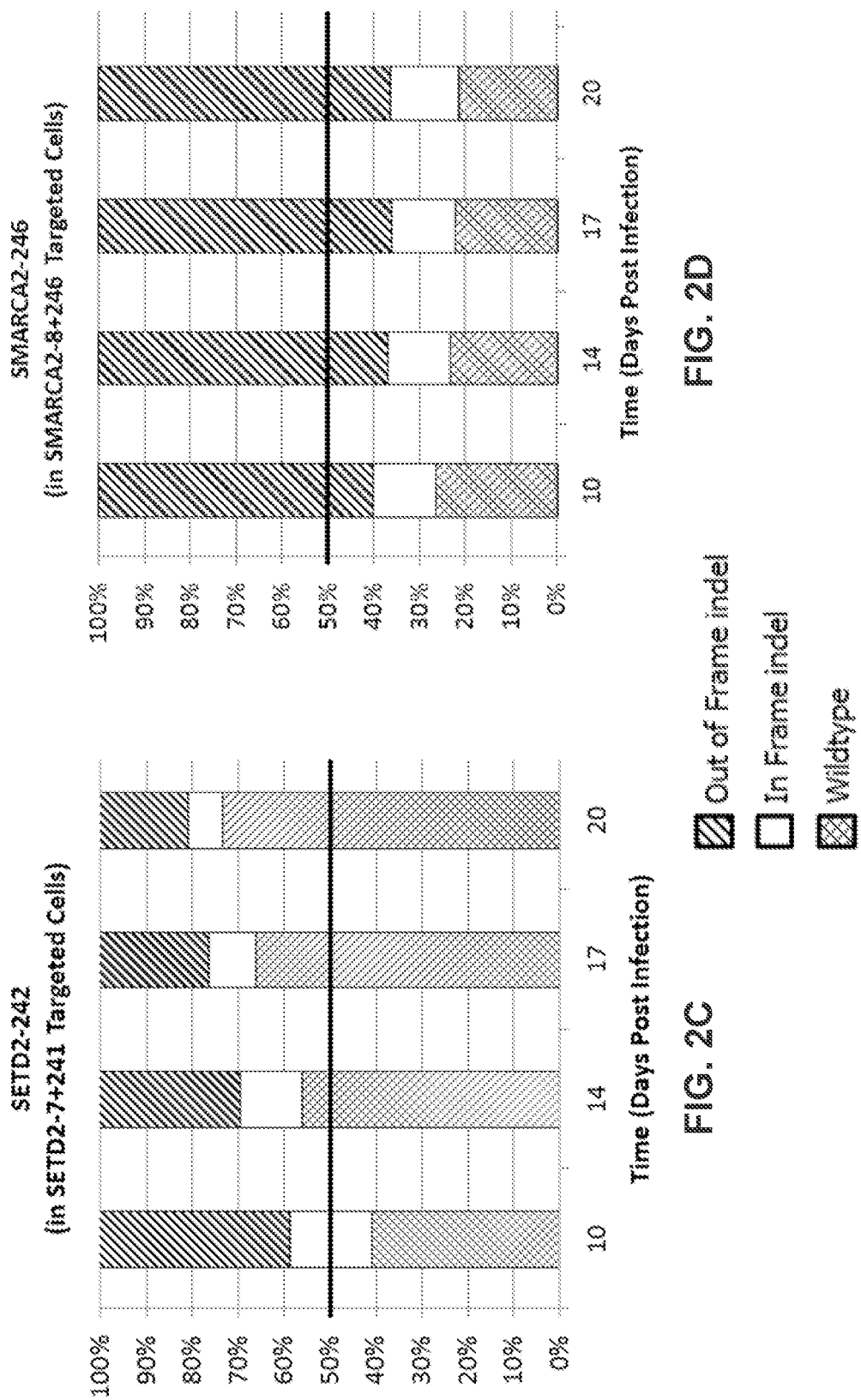

| Cell Line | Indication | EpiPool | EpiDomain Pool | Dual Assay | |
|---|---|---|---|---|---|
| | | | | Proliferation | NGS |
| OE21 | Esophageal | Sensitive | Sensitive | Sensitive | Sensitive |
| SW1990 | Pancreatic | Sensitive | Sensitive | Sensitive | Sensitive |
| SU8686 | Pancreatic | Sensitive | Sensitive | Sensitive | Sensitive |
| HUP-T4 | Pancreatic | Sensitive | Sensitive | Sensitive | Sensitive |
| CAPAN2 | Pancreatic | Sensitive | Sensitive | No Data | No Data |
| A549 | Lung | Insensitive | Insensitive | Insensitive | Insensitive |
| RKO | Colon | Insensitive | Insensitive | Insensitive | Insensitive |
| KP4 | Pancreatic | Insensitive | No Data | Insensitive | Insensitive |
| HPAF-II | Pancreatic | Insensitive | No Data | Insensitive | Inconclusive |

FIG. 4

METHODS OF TREATING CANCER BY INHIBITING SETD2

REFERENCE TO SEQUENCE LISTING SUBMITTED ELECTRONICALLY

The content of the electronically submitted sequence listing in ASCII text file (Name 3562.012000_Sequence_listing_ST25.txt; Size: 1,142 bytes; and Date of Creation: Aug. 14, 2017), filed with the application, is incorporated herein by reference in its entirety.

FIELD OF DISCLOSURE

The disclosure relates generally to the field of epigenetic-based cancer therapy. More particularly, the present disclosure relates to methods and pharmaceutical compositions for treating cancer by inhibiting the human histone methyltransferase, SETD2.

BACKGROUND

The selective addition of methyl groups to specific amino acid sites on histones is controlled by the action of a family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

SETD2 is a human histone methyltransferase that is located at the cytogenic band p21.31 of chromosome 3 (3p21.31). The acronym "SETD2" stands for Suppressor of variegation, Enhancer of zeste, and Trithorax domain containing 2. The SETD2 protein comprises three conserved functional domains: (1) the triplicate AWS-SET-PostSET domain; (2) a WW domain; and (3) a Set2-Rbp1 interacting ("SRI") domain. These three functional domains define the biological function of SETD2. See, Li, J. et al., *Oncotarget* 7:50719-50734 (2016). SETD2 is believed to be the single human gene responsible for the trimethylation of lysine 36 (Lys-36) of histone H3 (H3K36me3) using dimethylated Lys-36 (H3K36me2) as substrate. Edmunds, J. W. et al., *The EMBO Journal* 27:406-420 (2008).

Notably, human SETD2 has been shown to have tumor suppressor functionality. Li, J. et al., *Oncotarget* 7:50719-50734 (2016). For example, inactivation of human SETD2 has been reported in renal cell carcinoma (RCC). Larkin, J., et al., *Nature Reviews* 9:147-155 (2012). Also, expression levels of SETD2 in breast cancer samples have been reported as significantly lower than in adjacent non-cancerous tissue (ANCT) samples. Newbold, R. F. and Mokbel, K., *Anticancer Research* 30: 3309-3311 (2010). Additionally, biallelic mutations and loss-of-function point mutations in SETD2 were reported in patients with acute leukemia. Zhu, X. et al., *Nature Genetics* 46: 287-293 (2014). Mutations in SETD2 have also been reported in pediatric high-grade gliomas. Fontebasso, A. M. et al., *Acta Neuropathol.* 125: 659-669 (2013).

Despite more than a century of dedicated scientific and clinical research, curing cancer remains one of the biggest medical challenges to date. Cancer treatments have mainly relied on the combination of surgery, radiotherapy, and/or cytotoxic chemotherapies. And while effective cancer therapies exist, suboptimal response, relapsed-refractory disease, and/or resistance to one or more therapeutic agents have remained a challenge. Accordingly, there is a medical need for more effective, safe, and durable therapies for the treatment of all types of cancer.

SUMMARY

The present disclosure relates to the surprising and unexpected discovery that inhibiting human SETD2, despite its known functionality as a tumor suppressor, can be used to treat cancer, and pancreatic cancer and esophageal cancer in particular.

In one aspect, the present disclosure is directed to a method of treating cancer, comprising administering to a subject in need thereof a therapeutically effective amount of a SETD2 inhibitor.

In one aspect, the present disclosure is directed to a method of reducing or inhibiting proliferation of a cancer cell, comprising (i) contacting a cancer cell with an effective amount of a SETD2 inhibitor; and (ii) reducing or inhibiting proliferation of said cancer cell.

In certain embodiments, the SETD2 inhibitor is selected from the group consisting of a polypeptide, DNA, and RNA.

In certain embodiments, the SETD2 inhibitor is (i) an isolated binding molecule that specifically binds to a SETD2 polypeptide; (ii) an isolated binding molecule that specifically binds to a ligand of a SETD2 polypeptide; or (iii) an antisera raised against a SETD2 polypeptide.

In certain embodiments, the SETD2 inhibitor is an antibody or antigen binding fragment of an antibody that specifically binds to a SETD2 polypeptide. In certain embodiments, the antibody is a polyclonal, monoclonal, murine, human, humanized, or chimeric antibody. In certain embodiments, the antigen binding fragment is a Fab, Fab', F(ab')2, Fv, scFv, sdFv fragment, VH domain, or VL domain.

In certain embodiments, the SETD2 inhibitor is an RNAi, miRNA, siRNA, shRNA, an antisense RNA, an antisense DNA, a decoy molecule, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof, that hybridizes to a nucleotide sequence encoding a SETD2 polypeptide under a stringent condition, or a gene editing system. In certain embodiments, the SETD2 inhibitor is an siRNA selected from the group consisting of SEQ ID NOS: 1-4. In certain embodiments, the gene editing system is CRISPR/Cas9.

In certain embodiments, the SETD2 inhibitor is a small molecule compound. In certain embodiments, the small molecule compound is a sinefungin derivative selected from the group consisting of N-propyl sinefungin and N-benzyl sinefungin.

In certain embodiments, the cancer or cancer cell is selected from the group consisting of adrenal cancer, acinic cell carcinoma, acoustic neuroma, acral lentigious melanoma, acrospiroma, adenocarcinoma, adenoid cystic carcinoma, adenoma, adenomatoid odontogenic tumor, adenosquamous carcinoma, adipose tissue neoplasm, adrenocortical carcinoma, AIDS-related lymphoma, alveolar rhabdomyosarcoma, alveolar soft part sarcoma, ameloblastic fibroma, anaplastic large cell lymphoma, anaplastic thyroid cancer, angiomyolipoma, angiosarcoma, astrocytoma, atypical teratoid rhabdoid tumor, basal cell carcinoma, biliary tract cancer, bladder cancer, blastoma, bone cancer, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, dysembryoplastic neuroepithelial tumor, dysgerminoma, embryonal carcinoma, endocrine gland neoplasm, endodermal sinus tumor, esophageal cancer, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hepatoblastoma, hepatocellular carcinoma, hepatosplenic T-cell lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, liver cancer, small cell lung cancer, non-small cell lung cancer, malignant fibrous histiocytoma, malignant peripheral nerve sheath tumor, malignant triton tumor, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, papillary thyroid cancer, paraganglioma, pinealoblastoma, pineocytoma, pituicytoma, pituitary adenoma, pituitary tumor, plasmacytoma, polyembryoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, rectal cancer, sarcoma, Schwannomatosis, seminoma, Sertoli cell tumor, sex cord-gonadal stromal tumor, skin cancer, small cell carcinoma, soft tissue sarcoma, somatostatinoma, spinal tumor, squamous cell carcinoma, synovial sarcoma, small intestine cancer, squamous carcinoma, stomach cancer, testicular cancer, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Warthin's tumor, Wilms' tumor, squamous cell carcinoma of the head and neck, adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In certain embodiments, the cancer is pancreatic cancer or the cancer cell is derived from pancreatic cancer, or the cancer is esophageal cancer or the cancer cell is derived from esophageal cancer.

In certain embodiments, the cancer or cancer cell is selected from the group consisting of esophageal cancer, kidney cancer, stomach cancer, hepatocellular carcinoma, glioblastoma, central nervous system (CNS) cancer, soft tissue cancer, lung cancer, breast cancer, bladder/urinary tract cancer, head and neck cancer, prostate cancer, hematological cancer, pancreatic cancer, skin cancer, endometrial cancer, ovarian cancer, and colorectal cancer.

In certain embodiments, the cancer or cancer cell is a hematological cancer or the cancer cell is derived from a hematological cancer.

In certain embodiments, the hematological cancer is selected from the group consisting of acute lymphocytic leukemia (ALL), acute myeloid leukemia (AML), chronic lymphocytic leukemia (CLL), small lymphocytic lymphoma (SLL), multiple myeloma (MM), Hodgkins lymphoma (HL), non-Hodgkin's lymphoma (NHL), mantle cell lymphoma (MCL), marginal zone B-cell lymphoma, splenic marginal zone lymphoma, follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), Richter's transformation, acute eosinophilic leukemia, acute erythroid leukemia, acute lymphoblastic leukemia, acute megakaryoblastic leukemia, acute monocytic leukemia, acute promyelocytic leukemia, acute myelogeous leukemia, B-cell prolymphocytic leukemia, B-cell lymphoma, MALT lymphoma, precursor T-lymphoblastic lymphoma, T-cell lymphoma, mast cell leukemia, adult T cell leukemia/lymphoma, aggressive NK-cell leukemia, and angioimmunoblastic T-cell lymphoma.

In certain embodiments, the subject is a mammal. In certain embodiments, the subject is a human.

In certain embodiments, the SETD2 inhibitor is formulated for systemic or local administration. In certain embodiments, the SETD2 inhibitor is formulated for oral, nasal, intra-peritoneal, or intra-tumoral administration. In certain embodiments, the SETD2 inhibitor is formulated for intravenous administration, intramuscular administration, or subcutaneous administration.

In certain embodiments, the method further comprises the step of administering one or more additional therapeutic agents.

In certain embodiments, the SETD2 inhibitor is inhibits the trimethylation of lysine 36 on histone H3 (H3K36me3).

In one aspect, the present disclosure is directed to a SETD2 inhibitor for use in a method of treating cancer.

In one aspect, the present disclosure is directed to a method for treating cancer comprising inhibiting an activity of SETD2 in a subject in need thereof.

BRIEF DESCRIPTION OF THE DRAWINGS

FIG. 1B shows cell lines originating from pancreatic ductal adenocarcinoma (PDAC), which indicates that PDAC appears to show significant sensitivity to SETD2 depletion.

FIGS. 2A-2D provide an example of CRISPR pooled screen validation showing that the PDAC derived cell line, SU8686, is dependent on human SETD2 based on a dual sgRNA assay. The SMARCA2 gene was also targeted as a negative control. FIG. 2A is a schematic representation of the human SETD2 protein (having 2564 amino acids) indicating the functional domains (AWS, SET, PS, LCR, WW, SRI). The relative positions of target sites within the SETD2 gene are represented by the sgRNAs targeting those sites (sg_7, sg_9, sg 241, and sg_242). Three sites of the SETD2 gene were targeted, including the active site within the SET domain which was targeted with sg_241 or and/or sg_242. FIG. 2B is a graph showing the effect of dual sgRNA targeting of either SETD2 or SMARCA2 within the SU8686 cell line. The y-axis represents the fold-change in cell number (log 10-scale) and the x-axis represents days post infection. Combinations of sgRNAs wherein at least one of the two sgRNAs targeting the active site of SETD2 (i.e., sg 241 or sg_242) were included were found to have a dramatic effect on the proliferation of this cell line. In contrast, sgRNAs only targeting regions outside of the SETD2 active site (sg_7 and sg_9) did not affect cell proliferation. Likewise, sgRNAs that inactivated a negative control, SMARCA2, had no effect on proliferation. FIG. 2C is a bar chart representing the genotypes of cells that survived infection with SETD2-targeting sgRNAs (sg_7 and sg_241) over time. Next-generation sequencing (NGS) of sgRNA cut sites was used to genotype the surviving cells as either wild-type, or having an in-frame or an out-of-frame insertion or deletion ("indel"). This bar chart shows that in SETD2 sgRNA infected cells, the wild-type (uncut) population of alleles increases over time, indicating that cells with functional SETD2 have a survival advantage over cells with non-functional SETD2. FIG. 2D is a bar chart representing the genotypes of cells that survive infection with SMARCA2 sgRNAs (negative control) over time. This bar chart shows that the genotype associated with SMARCA2 sgRNAs remains constant over time, indicating that SMARCA2 activity is not required for SU8686 viability and growth.

FIG. 3A is a schematic representation of the human SETD2 protein (having 2564 amino acids) indicating the functional domains (AWS, SET, PS, LCR, WW, SRI). FIG. 3B is a bar graph showing the percent depletion from a screen utilizing sgRNAs targeting the entire length of the SETD2 gene. The data indicate that the SET domain and other domains that are important for the function of the encoded protein (including the "associated with SET" (AWS) domain) are depleted at a higher rate than other regions of the protein. This is due to the fact that functional domains have a much lower tolerance for mutations than other regions. These data strongly support the hypothesis that targeting the SET domain/active site of SETD2 with a small molecule inhibitor will result in a growth phenotype (i.e., reduced proliferation) in this esophageal cancer cell line.

FIG. 4 is a Table summarizing target validation efforts for the CRISPR screening assays. Representative cell lines are indicated in the first column. The results indicate whether the cell line is sensitive or insensitive to SETD2 depletion. CRISPR pooled screening results for selected cell lines are shown in the "Epipool column." Domain specific CRISPR pooled screening results are shown in the "Epidomain pool column." These results indicate that the SET domain for SETD2 is required for the effect. Validation of CRISPR pooled screening results in cell lines by dual sgRNA CRISPR assay targeting SETD2 and NGS confirmation (as shown in FIG. 2) are shown in the "Proliferation" and "NGS" columns. Boxes marked as ▨ are sensitive; boxes in grey are insensitive; boxes marked as ▨ indicate inconclusive results; boxes in white indicate that data are not available.

DETAILED DESCRIPTION

Definitions

Figure 1A:
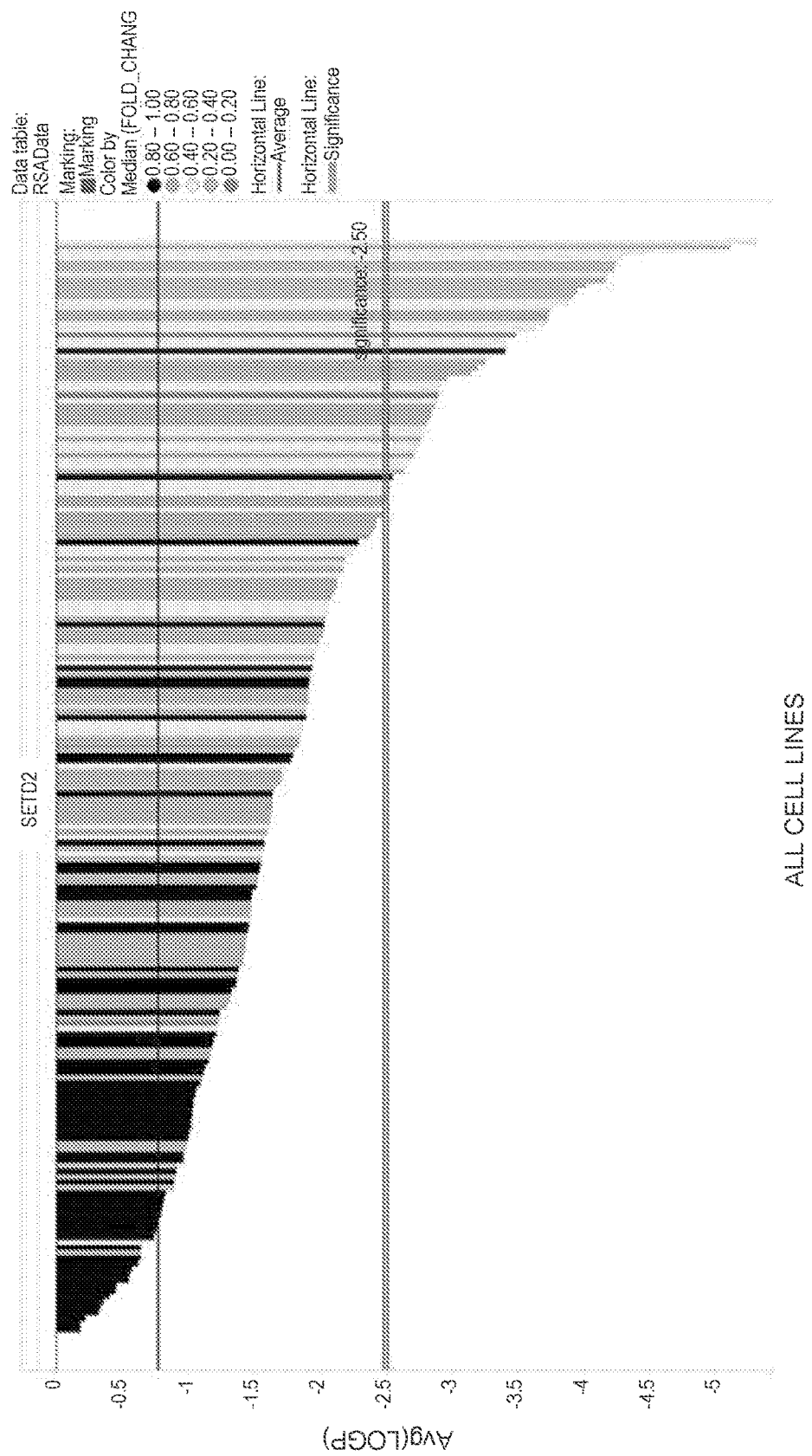
FIGS. 1A-1B are bar charts showing the results of a CRISPR pooled library screen targeting various genes, including SETD2. Cell lines, listed in Table 1 for FIG. 1A and on the x-axis of FIG. 1B, were infected with a pooled lentivirus library, wherein each lentivirus plasmid comprised a polynucleotide encoding a CRISPR-associated Cas9 polypeptide and a polynucleotide encoding a single guide RNA (sgRNA). Each bar on the graphs represents a human cancer cell line (with the exception of one control cell line, MCF10A, in FIG. 1A), and the LogP score on the Y-axis represents the depletion of a particular target from the population. Thus, the LogP score refers to the dependence of each cell line on a particular gene. In this case, each cell line with a LogP score below 2.5 is dependent on SETD2 for survival. The data for all 250 cell lines tested is presented in Table 1 and plotted in FIG. 1A. Sensitivity to SETD2 depletion was shown by cell lines originating from cancers of the breast, esophagus, kidney, lung, stomach, bladder/urinary tract, endometrium, skin, hematopoietic system (i.e., DLBCL and AML), soft tissue, CNS, pancreas, and ovary.

To facilitate an understanding of the present invention, a number of terms and phrases are defined below.

Open terms such as "include," "including," "contain," "containing" and the like mean "comprising." These open-ended transitional phrases are used to introduce an open ended list of elements, method steps, or the like that does not exclude additional, unrecited elements or method steps. Wherever aspects are described herein with the language "comprising," otherwise analogous aspects described in terms of "consisting of" and/or "consisting essentially of" are also provided.

As used in the present disclosure and claims, the singular forms "a," "an," and "the" include plural forms unless the context clearly dictates otherwise. For example, "a cell" includes a single cell as well as a plurality of cells, including mixtures thereof.

The term "SETD2" (also known as SET Domain Containing 2, Huntingtin-Interacting Protein B, Lysine N-Methyltransferase 3A, Huntingtin Yeast Partner B, EC 2.1.1.43, P231HBP, HIP-1, HIF-1, KMT3A, HYPB, SET2, Histone-Lysine N-Methyltransferase SETD2, Huntingtin Interacting Protein 1, Huntingtin-Interacting Protein 1, SET Domain-Containing Protein 2, KIAA1732, HSPC069, HBP231, HSET2, HIF 1, and LLS) refers to native histone methyltransferase SETD2, unless otherwise indicated. "Human SETD2" refers to native human histone methyltransferase SETD2. "SETD2" encompasses full-length, unprocessed SETD2, as well as any form of SETD2 that results from processing within the cell. The term also encompasses naturally occurring variants of SETD2, e.g., splice variants, allelic variants, and isoforms. SETD2 can be isolated from a variety of sources, e.g., from human tissue types or other animal tissue types, or prepared by recombinant or synthetic methods. Examples of human gene sequences encoding SETD2 or SETD2 polypeptide sequences include, but are not limited to, NCBI Gene ID 29072, HGNC: 18420, and SETD2 transcript variant 1, mRNA-NCBI Reference Sequence: NM_014159.6. The human gene encoding SETD2 is located on the short arm of chromosome 3. While the term "SETD2," as used herein, generally refers to the gene encoding human SETD2, other mammalian forms of SETD2 are contemplated as well.

As used herein, a "functional domain of SETD2" refers to one of the three conserved functional domains of SETD2 that are believed to define the biological function of SETD2. These functional domains are (1) the triplicate AWS-SET-PostSET domain; (2) a WW domain; and (3) a Set2-Rbp1 interacting ("SRI") domain (Li, J. et al., *Oncotarget* 7:50719-50734 (2016)), which can be described as follows:

AWS-SET-PostSETdomain. Without wishing to be bound by any theory, it is believed that the human SET domain is a motif of 130 amino acids that is evolutionarily conserved from yeast to mammals and is also found in some bacteria and viruses. The SET domain is usually present as part of a multi-domain, flanked by an AWS (Associated with SET) and a PostSET domain. Generally, SET-domain-containing proteins transfer one or several methyl groups from S-adenosyl-L-methionine to the amino group of a lysine or an arginine residue of histones or other proteins. It is believed that this transfer is dependent on the flanking AWS and PostSET regions, which contain several conserved cysteine residues. In contrast to other methyltransferases, SET-domain-containing methyltransferases have an α-sheet structure that facilitates multiple rounds of methylation without substrate disassociation.

WW domain. The "WW domain" refers to the presence of two conserved tryptophan (W) residues spaced 20-22 amino acids apart. Binding assays show that the WW domain preferentially binds to proline-rich segments, mediating protein-protein interactions to participate in a variety of molecular processes. Without wishing to be bound by any theory, it is believed that the WW domain recognizes motifs like Proline-Proline-x-Tyrosine (PPxY), phospho-Serine-Proline (p-SP) or phospho-Threonine-Proline (p-ST), and mediates protein binding. Aberrant expression of WW-domain-containing genes has been associated with diseases such as HD, Alzheimer's disease, and multiple cancer subtypes. Without wishing to be bound by any theory, it is believed that the WW domain in the C-terminal region of SETD2 interacts with the Huntingtin protein via its proline-rich segment, regardless of the length of the HD-associated polyglutamine track, and may also interact with TP53. SETD2 contains a proline-rich stretch that precedes the WW domain. This proline-rich stretch functions as an intramolecular WW-interacting domain that can block the WW domain of SETD2 from interacting with the proline-rich stretch of Huntingtin, and most likely of other proteins as well.

SRI domain. Without wishing to be bound by any theory, it is believed that the Set2 Rpb 1 Interacting ("SRI") domain interacts with the hyperphosphorylated C-terminal domain (CTD) of Rpbl, the largest subunit of RNA Pol II. Also without wishing to be bound by any theory, it is believed that in humans, the primary C-terminal domain-docking site of RNA Pol II is located at the first and second helices of SETD2. This domain is believed to direct the activity of SETD2 towards actively transcribed genes.

The phrase "substantially similar," or "substantially the same," as used herein, denotes a sufficiently high degree of similarity between two numeric values such that one of skill in the art would consider the difference between the two values to be of little or no biological and/or statistical significance within the context of the biological characteristics measured by said values (e.g., $K_d$ values).

A polypeptide, antibody, polynucleotide, vector, cell, or composition which is "isolated" is a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

"Polynucleotide" or "nucleic acid," as used interchangeably herein, refer to polymers of nucleotides of any length, and include both DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the present disclosure are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection.

Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.* 87:2264-2268 (1990), as modified in Karlin et al., *Proc. Natl. Acad. Sci.* 90:5873-5877 (1993), and incorporated into the NBLAST and)(BLAST programs (Altschul et al., *Nucleic Acids Res.* 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology* 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)), can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second amino acid sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be larger than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present disclosure, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence, for example.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Tumor" and "neoplasm" refer to any mass of tissue that results from excessive cell growth or proliferation, either benign (noncancerous) or malignant (cancerous) including pre-cancerous and in situ lesions.

The terms "cancer," "cancerous," or "malignancy," are used interchangeably, and refer to the physiological condition in mammals (i.e., humans) in which a population of cells are characterized by uncontrolled or unregulated cell growth or proliferation. Examples of cancer include, e.g., carcinoma, lymphoma, blastoma, sarcoma, myeloma, and leukemia. Non-limiting examples of cancer types that may be treated with the methods and pharmaceutical compositions of the present disclosure include esophageal cancer, kidney cancer, stomach cancer, hepatocellular carcinoma, glioblastoma, central nervous system (CNS) cancer, soft tissue cancer, lung cancer, breast cancer, bladder/urinary tract cancer, head and neck cancer, prostate cancer, hematological cancer, pancreatic cancer, colorectal cancer, skin cancer, endometrial cancer, ovarian cancer, and colorectal cancer.

The term "relapsed" cancer in a patient refers to patients who have previously achieved either a complete or partial remission, but after a period of 6 or more months, demonstrate evidence of disease progression.

The term "refractory" cancer in a patient refers to patients who have experienced treatment failure or disease progression within 6 months from the last anti-cancer therapy.

A tumor which "does not respond" or "responds poorly" to treatment (with, for example, a particular chemotherapeutic regimen) does not show statistically significant improvement in response to that treatment when compared to no treatment or treatment with a placebo in a recognized animal model or human clinical trial, or which responds to an initial treatment, but grows as treatment continues.

The term "pharmaceutical formulation" refers to a preparation that is in such a form as to permit the biological activity of the active ingredient(s) to be effective, and which contains no additional components which are unacceptably toxic to a subject to which the formulation would be administered. Such a formulation can be sterile.

The term "therapeutically effective amount" refers to the amount of a therapeutic agent (e.g., a small molecule inhibitor of SETD2) that is effective to "treat" a disease or disorder in a subject or mammal. In the case of cancer, the therapeutically effective amount of the agent can reduce the number of cancer cells, reduce the proliferation of cancer cells, reduce the tumor size, inhibit (i.e., slow to some extent and in some embodiments, stop) cancer cell infiltration into peripheral organs, inhibit (i.e., slow to some extent and in some embodiments, stop) tumor metastasis, inhibit, to some extent, tumor growth, and/or relieve to some extent one or more of the symptoms associated with the cancer. See the definition herein of "treating." To the extent the agent can prevent growth and/or kill existing cancer cells, it can be cytostatic and/or cytotoxic.

The term "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount may be less than the therapeutically effective amount.

Terms such as "treating," "treatment," "to treat," "having a therapeutic effect," "alleviating," "to alleviate," or "slowing the progression of" refer to both 1) therapeutic measures that cure, eradicate, slow down, lessen symptoms of, and/or halt progression of a diagnosed pathologic disorder, such as cancer; and 2) prophylactic or preventative measures that prevent and/or slow the development of cancer. Thus, those in need of treatment include those already with the disorder; those prone to have the disorder; and those in whom the disorder is to be prevented. In certain embodiments, a subject is successfully "treated" for cancer, according to the methods of the present disclosure, if the patient shows one or more of the following: reduction in cachexia, increase in survival time, elongation in time to tumor progression, reduction in tumor mass, reduction in tumor burden and/or a prolongation in time to tumor metastasis, time to tumor recurrence or progressive disease, tumor response, complete response (CR), partial response (PR), stable disease, progression free survival (PFS), overall survival (OS), each as measured by standards set by the National Cancer Institute and the U.S. Food and Drug Administration (FDA) for the approval of new drugs. See, Johnson et al, *J. Clin. Oncol.* 21:1404-1411 (2003). In some embodiments, the "therapeutic effect," as defined above, also encompasses a reduction in toxicity or adverse side effects, and/or an improvement in tolerability.

"Administering" refers to the physical introduction of a SETD2 inhibitor as described herein (and/or one or more additional therapeutic agents) to a subject, using any of the various methods and delivery systems known to those skilled in the art. Routes of administration include oral, mucosal, topical, intravenous, intramuscular, subcutaneous, intraperitoneal, spinal, or other parenteral routes of administration, for example, by injection or infusion. As used herein, the phrase "parenteral administration" means modes of administration including, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Administering can be performed, for example, once, a plurality of times, and/or over one or more extended periods.

The term "combination of agents," such as the combination of a SETD2 inhibitor and one or more other therapeutic agents refers to the administration of these agents to the same subject simultaneously, sequentially, or both simultaneously and sequentially. By way of example, administration of a SETD2 inhibitor preceding or following (e.g., by hour(s), day(s), week(s), or month(s)) administration of another therapeutic agent, constitutes administration of a combination of agents, regardless of whether the agents are administered together in a single pharmaceutical formulation or are administered in separate pharmaceutical formulations by either the same or different routes of administration.

The term "reducing or inhibiting proliferation of a cancer cell," as used herein, refers to the in vitro, ex vivo, or in vivo decrease in growth of one or more cells originating from a mammalian (e.g., human) cancer, as described herein.

All numbers in this disclosure indicating amounts, ratios, physical properties of materials, and/or use are to be understood as modified by the word "about," except as otherwise indicated. The term "about," when referring to a number or numerical range, means that the number or range referred to is an approximation, e.g., within experimental variability (or within statistical experimental error), and thus, the number or numerical range can vary from, e.g., between 1% and 15% of the stated number or numerical range.

SETD2 Inhibitors

The present disclosure provides an innovative treatment for subjects with cancer. The present disclosure relates to the surprising and unexpected discovery that inhibiting the histone methyltransferase, SETD2, despite its known functionality as a tumor suppressor, can be used to treat cancer, and pancreatic cancer and esophageal cancer in particular.

The treatment includes, inter alia, administering to a subject in need thereof a therapeutically effective amount of an inhibitor of the histone methyltransferase, SETD2, and treating the cancer.

As used herein, the term "an inhibitor of SETD2" or "a SETD2 inhibitor" refers to any molecule or compound that modulates, e.g., downregulates, an activity of human SETD2. For example, a SETD2 inhibitor may inhibit histone methyltransferase activity of SETD2. For instance, a SETD2 inhibitor can be a compound that exhibits a biochemical 50% inhibitory concentration ($IC_{50}$) with respect to SETD2 in a purified enzyme assay of between about 1 nM and about 10,000 nM, between about 1 nM and about 1,000 nM, between about 1 nM and about 500 nM, between about 1 nM and about 100 nM, between about 1 nM and about 50 nM, or between about 1 nM and about 10 nM.

In some embodiments, "downregulating (or inhibiting) an activity of human SETD2" refers to inhibiting trimethylation of the lysine 36 of histone 3.

In some embodiments, the SETD2 inhibitor can be, for example, a polypeptide, DNA, or RNA. The inhibitor of SETD2 can also be, for example, a molecule that specifically binds to a SETD2 polypeptide, a molecule that specifically binds to a ligand of a SETD2 polypeptide, an antisera raised against a SETD2 polypeptide, a soluble SETD2 polypeptide, or a soluble SETD2 polypeptide comprising, consisting essentially of, or consisting of an extracellular domain of a SETD2 polypeptide.

In some embodiments, the SETD2 inhibitor can also be, for example, an antibody that specifically binds to a SETD2 polypeptide or an antigen binding fragment of an antibody that specifically binds to a SETD2 polypeptide. In some embodiments, the antibody is a polyclonal, monoclonal, murine, human, humanized, or chimeric antibody. Monoclonal and polyclonal anti-SETD2 antibodies are commercially available and may be purchased, for example, from Thermo Fisher Scientific and Millipore Sigma. In some embodiments, the antigen binding fragment is a Fab, Fab', F(ab')2, Fv, scFv, sdFv fragment, VH domain, or VL domain.

In some embodiments, the SETD2 inhibitor can also be, for example, an RNAi, miRNA, siRNA, shRNA, antisense RNA, antisense DNA, decoy molecule, decoy DNA, double-stranded DNA, single-stranded DNA, complexed DNA, encapsulated DNA, viral DNA, plasmid DNA, naked RNA, encapsulated RNA, viral RNA, double-stranded RNA, molecule capable of generating RNA interference, or combinations thereof, that hybridizes to a nucleotide sequence encoding a SETD2 polypeptide.

Downregulation of SETD2 can also be achieved by gene editing technologies. In some embodiments, the SETD2 inhibitor can be, for example, a clustered regularly interspaced short palindromic repeat (CRISPR)-Cas9 system. CRISPR-Cas9 systems have been described in the literature with applications in cancer biology, and can include, for example, a Cas9 nuclease and a single guide RNA (sgRNA). See, Sanchez-Rivera, F. J. and Jacks, T., "Applications of the CRISPR-Cas9 System in Cancer Biology," *Nat Rev Cancer*

15: 387-395 (2015); Chen, S. et al., "CRISPR-Cas9: from Genome Editing to Cancer Research," Int. *J. Biol. Sci.* 12: 1427-1436 (2016). For example, a sgRNA targeting the SETD2 gene together with a Cas9 nuclease can be administered to a subject resulting in ablation of a particular sequence of the SETD2 gene resulting in downregulated SETD2 activity (i.e., inhibited trimethylation of lysine 36 of histone H3). In particular, the SET, AWS, PS, SRI, or WW domains could be targeted with CRISPR-Cas9 for ablation. A non-limiting example of a CRISPR-Cas9 system comprises an sgRNA Target Sequence #1 having the sequence AGCACCAGTAACAGAGCCAG (SEQ ID NO: 5), an sgRNA Target Sequence #2 having the sequence GACTGTGAACGGACAACTGA (SEQ ID NO: 6), and a Cas9 mRNA. In some embodiments, the sgRNAs and Cas9 mRNA may each be contained in separate vectors. In some embodiments, the sgRNAs may both be contained in a first vector and the Cas9 mRNA may be contained in a second vector. In some embodiments, the sgRNAs and the Cas9 mRNA may all be contained in a single vector. Those skilled in the art are aware of reagents and methods for formulating a CRISPR-Cas9 system for administration to a subject in need thereof.

In addition to CRISPR-Cas9-based systems, other alternative CRISPR-based systems can be used to inhibit SETD2, such as, e.g., the CRISPR/Cpf1 system of the bacterium *Francisella novicida*. See, Zetsche, B. et al., *Cell* 163:759-771 (2015); Fonfara, I et al., *Nature* 532: 517-521 (2016).

In addition to CRISPR-based systems, other gene editing techniques, such as, e.g., zinc finger nucleases (ZFNs), transcription activator-like effector nucleases (TALENs), and engineered homing meganucleases can also be used to inhibit SETD2. See, e.g., Maeder, M. L. and Gersbach, C. A., "Genome-editing Technologies for Gene and Cell Therapy," *Mol. Ther.* 24: 430-446 (2016); Gaj, T. et al., "ZFN, TALEN, and CRISPR/Cas-based methods for genome engineering," *Trends Biotechnol* 31:397-405 (2013); Perez-Pinera, P. et al., "Advances in targeted genome editing," *Curr Opin Chem Biol* 16:268-277 (2012).

In some embodiments, the SETD2 inhibitor used in the methods of the present disclosure is a small molecule (i.e., a molecule of molecular weight less than about 1,500 g/mol, e.g., between about 100 g/mol and about 1,500 g/mol) chemical compound that selectively targets and downregulates one or more activities of SETD2. In some embodiments, the small molecule inhibitor of SETD2 is a sinefungin derivative. Sinefungin is an analog of S-adenosylmethionine (SAM). In some embodiments, the sinefungin analog is an N-alkyl (methyl, ethyl, propyl, benzyl) sinefungin. In some embodiments, the N-alkyl sinefungin is N-propyl sinefungin (Pr-SNF) or N-benzyl sinefungin (Bn-SNF). The synthesis of sinefungin derivatives and their inhibition profile against the human methyltransferase SETD2 is described in Zheng, W. et al., *J. Am. Chem. Soc.* 134:18004-18014 (2012), which is incorporated by reference in its entirety.

In one embodiment, the SETD2 inhibitor is an antisense nucleic acid or oligonucleotide that is wholly or partially complementary to, and can hybridize with, a target nucleic acid encoding the SETD2 polypeptide (either DNA or RNA). For example, an antisense nucleic acid or oligonucleotide can be complementary to 5' or 3' untranslated regions, or can overlap the translation initiation codon (5' untranslated and translated regions) of at least one nucleic acid molecule encoding SETD2. As non-limiting examples, antisense oligonucleotides may be targeted to hybridize to the following regions: mRNA cap region, translation initiation site; translational termination site; transcription initiation site; transcription termination site; polyadenylation signal; 3' untranslated region; 5' untranslated region; 5' coding region, mid coding region; 3' coding region: DNA replication initiation and elongation sites.

In some embodiments, oligonucleotides can be constructed that will bind to duplex nucleic acid (i.e., DNA: DNA or DNA:RNA), to form a stable triple helix or triplex nucleic acid. Such triplex oligonucleotides can inhibit transcription and/or expression of a nucleic acid encoding SETD2. Triplex oligonucleotides are constructed using the base-pairing rules of triple helix formation.

In yet a further embodiment, oligonucleotides can be used in the present method that contain moieties having non-naturally-occurring portions. Thus oligonucleotides may have altered sugar moieties or inter-sugar linkages. Exemplary among these are phosphorothioate and other sulfur containing species which are known in the art. In preferred embodiments, at least one of the phosphodiester bonds of the oligonucleotide has been substituted with a structure that functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures.

In other embodiments, the phosphodiester bonds are substituted with structures which are, at once, substantially non-ionic and non-chiral, or with structures which are chiral and enantiomerically specific. Persons of ordinary skill in the art will be able to select other linkages for use in the disclosed methods, including inverted terminal nucleotides. Oligonucleotides may also include species that include at least some modified base forms. Thus, purines and pyrimidines other than those normally found in nature may be so employed. Similarly, modifications on the furanosyl portions of the nucleotide subunits may also be affected. Examples of such modifications are 2'-O-alkyl- and 2'-halogen-substituted nucleotides. Some non-limiting examples of modifications at the 2' position of sugar moieties include OH, SH, $SCH_3$, F, $OCH_3$, OCN, $O(CH_2)$, $NH_2$ and $O(CH_2)_n CH_3$, where n is from 1 to about 10. Such oligonucleotides are functionally interchangeable with natural oligonucleotides or synthesized oligonucleotides, which have one or more differences from the natural structure. All such analogs are comprehended herewith so long as they function effectively to hybridize with at least one nucleic acid molecule encoding SETD2 to inhibit the function thereof.

Alternatively, expression vectors derived from retroviruses, adenovirus, herpes or vaccinia viruses or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding a human SETD2 polypeptide.

RNA interference (RNAi) is a post-transcriptional gene silencing process that is induced by a miRNA or a dsRNA (a small interfering RNA; siRNA), and has been used to modulate gene expression. RNAi can be used in the therapeutic method describe herewith to inhibit SETD2. Generally, RNAi is being performed by contacting cells with a double stranded siRNA or a small hairpin RNA (shRNA). However, manipulation of RNA outside of cells is tedious due to the sensitivity of RNA to degradation. It is thus also encompassed herein deoxyribonucleic acid (DNA) compositions encoding small interfering RNA (siRNA) molecules, or intermediate siRNA molecules (such as shRNA), comprising one strand of an siRNA to be used. Accordingly, the present application provides an isolated DNA molecule, which includes an expressible template nucleotide sequence of at least about 16 nucleotides encoding an Intermediate siRNA, which, when a component of an siRNA, mediates RNA interference (RNAi) of a target RNA. The present application further concerns the use of RNA interference (RNAi) to modulate the expression of nucleic acid molecules encoding SETD2 in target cells. While the therapeutic applications are not limited to a particular mode of action, RNAi may involve degradation of messenger RNA (e.g., mRNA of genes of SETD2) by an RNA induced silencing complex (RISC), preventing translation of the transcribed targeted mRNA. Alternatively, it may also involve methylation of genomic DNA, which shuts down transcription of a targeted gene. The suppression of gene expression caused by RNAi may be transient or it may be more stable, even permanent.

"Small interfering RNA" (siRNA) can also be used in the present methods as a SETD2 inhibitor. siRNA refers to any nucleic acid molecule capable of mediating RNA interference (RNAi) or gene silencing. For example, siRNA can be double stranded RNA molecules from about 10 to about 30 nucleotides long that are named for their ability to specifically interfere with protein expression (e.g., SETD2 protein expression). In one embodiment, siRNAs of the present disclosure are 12-28 nucleotides long, more preferably 15-25 nucleotides long, even more preferably 19-23 nucleotides long, and most preferably 21-23 nucleotides long. Therefore, preferred siRNA are 12, 13, 14, 15, 16, 17, 18, 19, 20, 21, 22, 23, 24, 25, 26, 27, 28 nucleotides in length. As used herein, siRNA molecules need not to be limited to those molecules containing only RNA, but further encompass chemically modified nucleotides and non-nucleotides. siRNA can be designed to decrease expression of SETD2 in a target cell by RNA interference. siRNAs can comprise a sense region and an antisense region wherein the antisense region comprises a sequence complementary to an mRNA sequence for a nucleic acid molecule encoding SETD2 and the sense region comprises a sequence complementary to the antisense sequence of the gene's mRNA. An siRNA molecule can be assembled from two nucleic acid fragments wherein one fragment comprises the sense region and the second fragment comprises the antisense region of the siRNA molecule. The sense region and antisense region can also be covalently connected via a linker molecule. The linker molecule can be a polynucleotide linker or a non-polynucleotide linker.

In one embodiment, the SETD2 inhibitor is a human SETD2 siRNA selected from the group consisting of: SEQ ID NO: 1, SEQ ID NO: 2, SEQ ID NO: 3, and SEQ ID NO: 4.

```
UAAAGGAGGUAUAUCGAAU          (SEQ ID NO: 1)

GAGAGGUACUCGAUCAUAA          (SEQ ID NO: 2)

GCUCAGAGUUAACGUUUGA          (SEQ ID NO: 3)

CCAAAGAUUCAGACAUAUA          (SEQ ID NO: 4)
```

A ribozyme (from ribonucleic acid enzyme, also called RNA enzyme or catalytic RNA) is an RNA molecule that catalyzes a chemical reaction. Some ribozymes may play an important role as therapeutic agents, as enzymes which target defined RNA sequences, as biosensors, and for applications in functional genomics and gene discovery. Ribozymes can be genetically engineered to specifically cleave a transcript of a gene from a nucleic acid molecule encoding SETD2 whose expression is desired to be down-regulated.

The delivery of the gene or genetic material into the cell (encoding partly or wholly the sequence that will lower the expression of SETD2) is the first step in gene therapy treatment of any disorder. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

The use of RNA or DNA based viral systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells then administered to patients (ex vivo). Conventional viral based systems for the delivery of nucleic acids could include retroviral, lentiviral, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) are predominantly used in transient expression gene therapy; because they can be produced at high titer and they readily infect a number of different cell types. Most adenovirus vectors are engineered such that a transgene replaces the Ad E1a, E1b, and E3 genes; subsequently the replication defective vector is propagated in human 293 cells that supply the deleted gene function in trans. Ad vectors can transduce multiple types of tissues in vivo, including non-dividing, differentiated cells such as those found in the liver, kidney and muscle tissues. Conventional Ad vectors have a large carrying capacity.

In many gene therapy applications, it is desirable that the gene therapy vector be delivered with a high degree of specificity to a particular tissue type, such as for example, the glial cells. A viral vector is typically modified to have specificity for a given cell type by expressing a ligand as a fusion protein with a viral coat protein on the viruses outer surface. The ligand is chosen to have affinity for a receptor known to be present on the cell type of interest.

Gene therapy vectors can be delivered in vivo by administration to an individual subject, typically by systemic administration (e.g., intravenous, intratumoral, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, and tissue biopsy) or universal donor hematopoietic stem cells, followed by re-implantation of the cells into the subject, usually after selection for cells which have incorporated the vector.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft at an appropriate location (such as in the bone marrow). Methods for differentiating CD34+ cells in vitro into clinically important immune cell types using cytokines such as for example GM-CSF, IFN-γ and TNF-α are known.

Stem cells are isolated for transduction and differentiation using known methods. For example, stem cells can be isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells).

Administration of SETD2 Inhibitors

Suitable methods of administering the SETD2 inhibitors described herein will be based on the nature of the inhibitor (i.e., small molecule, DNA, RNA, protein, antibody) and are well known to those skilled in the art. The SETD2 inhibitors described herein may be administered by the oral, parenteral, subcutaneous, intravenous, intramuscular, intraperitoneal, transdermal, intrathecal, intranasal, transmucosal, intratumoral, rectal, intravaginal, or buccal route, or by inhalation. For example, intravenous injection such as drip infusion, intramuscular injection, intraperitoneal injection, subcutaneous injection, suppositories, intestinal lavage, oral enteric-coated tablets, and the like can be selected, and the method of administration may be chosen, as appropriate, depending on the age and condition of the patient. The SETD2 inhibitors described herein may be administered systemically (e.g., by intravenous injection) or locally (e.g., intrathecally, intratumorally, or into a lymph node).

The appropriate dosage of a SETD2 inhibitor of the present disclosure depends on several factors, such as, e.g., the type of cancer to be treated, the severity, course, and stage of the cancer, the responsiveness of the cancer, previous therapy, the patient's clinical history, and so on, all at the discretion of the treating physician. In some embodiments, the dosage of the SETD2 inhibitor is from about 0.01 mg/kg to about 1000 mg/kg of body weight. In some embodiments, the dosage of the SETD2 inhibitor is about 1 mg/kg to about 500 mg/kg of body weight. In some embodiments, the dosage of the SETD2 inhibitor is about 0.1 mg/day to about 50 g/day; about 0.1 mg/day to about 25 g/day; about 0.1 mg/day to about 10 g/day; about 0.1 mg/day to about 3 g/day; or about 0.1 mg/day to about 1 g/day. Alternatively, the dosage of the SETD2 inhibitor is in the range of 1 to 2000 mg, and preferably 100 to 1000 mg per patient.

In some embodiments, the SETD2 inhibitor can be administered one time or over a series of treatments lasting from several days to several months, or until a cure is effected or a diminution of the disease state is achieved (e.g., reduction in tumor size).

In some embodiments, the SETD2 inhibitors described herein can be given once or more daily, weekly, monthly, or yearly. In certain embodiments, the SETD2 inhibitor is given once every day, once every two days, once every three days, or once every four days. In certain embodiments, the SETD2 inhibitor is given twice per day, three times per day, or four times per day. In certain embodiments, the SETD2 inhibitor is given once a week. In certain embodiments, the SETD2 inhibitor is given once every two weeks. In certain embodiments, the SETD2 inhibitor is given once every three weeks. In some embodiments, the SETD2 inhibitor is given once every four weeks. In some embodiments, the SETD2 inhibitor is given once a month.

In some embodiments, the SETD2 inhibitors described herein may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) twice a day, once per day, once every two days, once every three days, or once every week. For example, a dosing regimen may comprise administering an initial loading dose, followed by a daily maintenance dose of, for example, one-half of the initial dose. Or a dosing regimen may comprise administering an initial loading dose, followed by maintenance doses of, for example one-half of the initial dose every other day. Or a dosing regimen may comprise administering three initial doses for 3 days, followed by maintenance doses of, for example, the same amount every other day.

One of ordinary skill in the art will appreciate that the dosage administered, route of administration, and frequency of administration will vary, depending upon the circumstances of the particular subject being treated, and taking into account such factors as age, gender, health, and weight of the recipient, condition or disorder to be treated, severity of the disorder, type of concurrent treatment(s), if any, and the nature of the effect desired.

One skilled in the art will also appreciate that the dosage of SETD2 inhibitor and/or frequency of administration may change during the course of therapy (lowered or increased) depending upon the patient's clinical response, side effects, etc., or during different phases of therapy (i.e., treatment or maintenance).

Pharmaceutical Compositions

The SETD2 inhibitors used in the methods described herein can be formulated into pharmaceutical compositions suitable for administration to subjects in need thereof (i.e., subjects afflicted with cancer). As used herein, a "pharmaceutical composition" refers to a preparation of one or more agents as described herein (e.g., a SETD2 inhibitor or a SETD2 inhibitor with one or more other therapeutic agents), or physiologically acceptable salts or prodrugs thereof, with other chemical components, including, but not limited to, pharmaceutically acceptable carriers, excipients, lubricants, buffering agents, antibacterial agents, bulking agents (e.g., mannitol), antioxidants (e.g., ascorbic acid or sodium bisulfite), and the like. The purpose of the pharmaceutical composition is to facilitate administration of the agent(s) to a subject.

The terms "pharmaceutically acceptable carrier", "excipients" and "adjuvant" and "physiologically acceptable vehicle" and the like are to be understood as referring to an acceptable carrier or adjuvant that may be administered to a patient, together with the SETD2 inhibitor described herein, and which does not destroy or abrogate the pharmacological activity thereof. A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are well known in the art (see, Remington: The Science and Practice of Pharmacy, 21$^{st}$ Edition, A. R. Gennaro (Lippincott, Williams & Wilkins, Baltimore, MDd. 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly(vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN® 80], sorbitan monopalmitate [SPAN® 40], glyceryl monooleate, polyoxyethylene esters, polyethylene glycol fatty acid esters (e.g., CREMOPHOR®), polyoxyethylene ethers (e.g., polyoxyethylene lauryl ether [BRIJ® 30]), PLUORINC® F 68, POLOXAMER® 188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here may contain a cyroprotectant to stabilize a polynucleotide described herein during freezing. Exemplary cryoprotectants include, but are not limited to mannitol, sucrose, trehalose, lactose, glycerol, dextrose, etc., and combinations thereof.

Administration of the SETD2 inhibitor of the present disclosure is by any of the routes normally used for introducing a molecule into ultimate contact with tumor cells. The pharmaceutical compositions comprising a SETD2 inhibitor can be administered by any suitable method, e.g., parenterally, intraventricularly, orally, topically, rectally, vaginally, nasally, buccally, or via an implanted reservoir. As used herein, the term "parenteral" includes subcutaneous, intravenous, intramuscular, intra-articular, intra-synovial, intrasternal, intrathecal, intrahepatic, intralesional and intracranial injection or infusion techniques.

Parenteral formulations can be a single bolus dose, an infusion, or a loading bolus dose followed with a maintenance dose. These compositions can be administered at specific fixed or variable intervals, e.g., twice a week or once a week. In some embodiments, the SETD2 inhibitor is administered intravenously.

In certain embodiments, the pharmaceutical compositions can be orally administered in an acceptable dosage form including, e.g., capsules, tablets, aqueous suspensions or solutions. In certain embodiments, the pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

Those skilled in the art will appreciate that specific dosage and treatment regimen for any particular patient will depend upon a variety of factors, including the particular therapeutic agents used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well-known in the art.

In some embodiments, the SETD2 inhibitor, as described herein, is administered in combination with one or more additional therapeutic agents and/or therapeutic procedures. In some embodiments, the SETD2 inhibitor, as described herein, can be co-formulated with and/or co-administered with one or more additional therapeutic agents. In some embodiments, the methods described herein further comprise administering to the subject at least one additional therapeutic agent.

Methods of Treating Cancer

In one aspect, the present disclosure provides a method of treating or slowing the progression of a cancer in a subject, by administering to the subject in need thereof a therapeutically effective amount of a SETD2 inhibitor, such as those described above.

Numerous types of cancers can be treated by the disclosed methods and pharmaceutical compositions. In some embodiments, the cancer is selected from the group consisting of adrenal cancer, acinic cell carcinoma, acoustic neuroma, acral lentigious melanoma, acrospiroma, adenocarcinoma, adenoid cystic carcinoma, adenoma, adenomatoid odontogenic tumor, adenosquamous carcinoma, adipose tissue neoplasm, adrenocortical carcinoma, AIDS-related lymphoma, alveolar rhabdomyosarcoma, alveolar soft part sarcoma, ameloblastic fibroma, anaplastic large cell lymphoma, anaplastic thyroid cancer, angiomyolipoma, angiosarcoma, astrocytoma, atypical teratoid rhabdoid tumor, basal cell carcinoma, biliary tract cancer, bladder cancer, blastoma, bone cancer, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, dysembryoplastic neuroepithelial tumor, dysgerminoma, embryonal carcinoma, endocrine gland neoplasm, endodermal sinus tumor, esophageal cancer, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hepatoblastoma, hepatocellular carcinoma, hepatosplenic T-cell lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, liver cancer, small cell lung cancer, non-small cell lung cancer, malignant fibrous histiocytoma, malignant peripheral nerve sheath tumor, malignant triton tumor, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, papillary thyroid cancer, paraganglioma, pinealoblastoma, pineocytoma, pituicytoma, pituitary adenoma, pituitary tumor, plasmacytoma, polyembryoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, rectal cancer, sarcoma, Schwannomatosis, seminoma, Sertoli cell tumor, sex cord-gonadal stromal tumor, skin cancer, small cell carcinoma, soft tissue sarcoma, somatostatinoma, spinal tumor, squamous cell carcinoma, synovial sarcoma, small intestine cancer, squamous carcinoma, stomach cancer, testicular cancer, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Warthin's tumor, Wilms' tumor, squamous cell carcinoma of the head and neck, adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In some embodiments, the cancer is esophageal cancer, kidney cancer, stomach cancer, hepatocellular carcinoma, glioblastoma, central nervous system (CNS) cancer, soft tissue cancer, lung cancer, breast cancer, bladder/urinary tract cancer, head and neck cancer, prostate cancer, hematological cancer, pancreatic cancer, skin cancer, endometrial cancer, ovarian cancer, or colorectal cancer.

In some embodiments, the cancer is pancreatic cancer. In some embodiments, the cancer is esophageal cancer.

In some embodiments, the cancer is a hematological cancer, selected from the group consisting of acute lymphocytic leukemia (ALL), acute myeloid leukemia (AML), chronic lymphocytic leukemia (CLL), small lymphocytic lymphoma (SLL), multiple myeloma (MM), Hodgkins lymphoma (HL), non-Hodgkin's lymphoma (NHL), mantle cell lymphoma (MCL), marginal zone B-cell lymphoma, splenic marginal zone lymphoma, follicular lymphoma (FL), Waldenstrom's macroglobulinemia (WM), diffuse large B-cell lymphoma (DLBCL), marginal zone lymphoma (MZL), hairy cell leukemia (HCL), Burkitt's lymphoma (BL), Richter's transformation, acute eosinophilic leukemia, acute erythroid leukemia, acute lymphoblastic leukemia, acute megakaryoblastic leukemia, acute monocytic leukemia, acute promyelocytic leukemia, acute myelogeous leukemia, B-cell prolymphocytic leukemia, B-cell lymphoma, MALT lymphoma, precursor T-lymphoblastic lymphoma, T-cell lymphoma, mast cell leukemia, adult T cell leukemia/lymphoma, aggressive NK-cell leukemia, and angioimmunoblastic T-cell lymphoma.

In some embodiments, the hematological cancer is selected from the group consisting of acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), mantle cell lymphoma (MCL), follicular lymphoma (FL), Waldenstrom's macroglobulinemia (WM), diffuse large B-cell lymphoma (DLBCL), marginal zone lymphoma (MZL), including extranodal and nodal MZL, hairy cell leukemia (HCL), Burkitt's lymphoma (BL), and Richter's transformation.

In some embodiments, the cancer is refractory to traditional chemotherapy.

In some embodiments, the cancer has relapsed.

The SETD2 inhibitor (alone or in combination with one or more additional therapeutic agents or therapeutic procedures) used in the methods described herein can be administered in any order or at any interval as determined by those skilled in the art.

In some embodiments, treatment by the methods described herein can last indefinitely (i.e., as a maintenance therapy). In some embodiments, treatment by the methods described herein can last up to about 18 weeks, up to about 17 weeks, up to about 16 weeks, up to about 15 weeks, up to about 14 weeks, up to about 13 weeks, or up to about 12 weeks. In some embodiments, treatment lasts about 12 weeks. In some embodiments, treatment by the methods described herein can last between about 1 week and about 52 weeks, between about 1 week and about 26 weeks, between about 1 week and about 12 weeks, between about 1 week and about 6 weeks, between about 6 weeks and about 52 weeks, between about 6 weeks and about 26 weeks, or between about 12 weeks and about 52 weeks. In some embodiments, treatment by the methods described herein can last more than 52 weeks.

The present invention is further illustrated by the following example which should not be construed as further limiting. The contents of all patent and non-patent references cited throughout this application are expressly incorporated herein by reference in their entireties.

EXAMPLES

Example 1

Figure 1B:
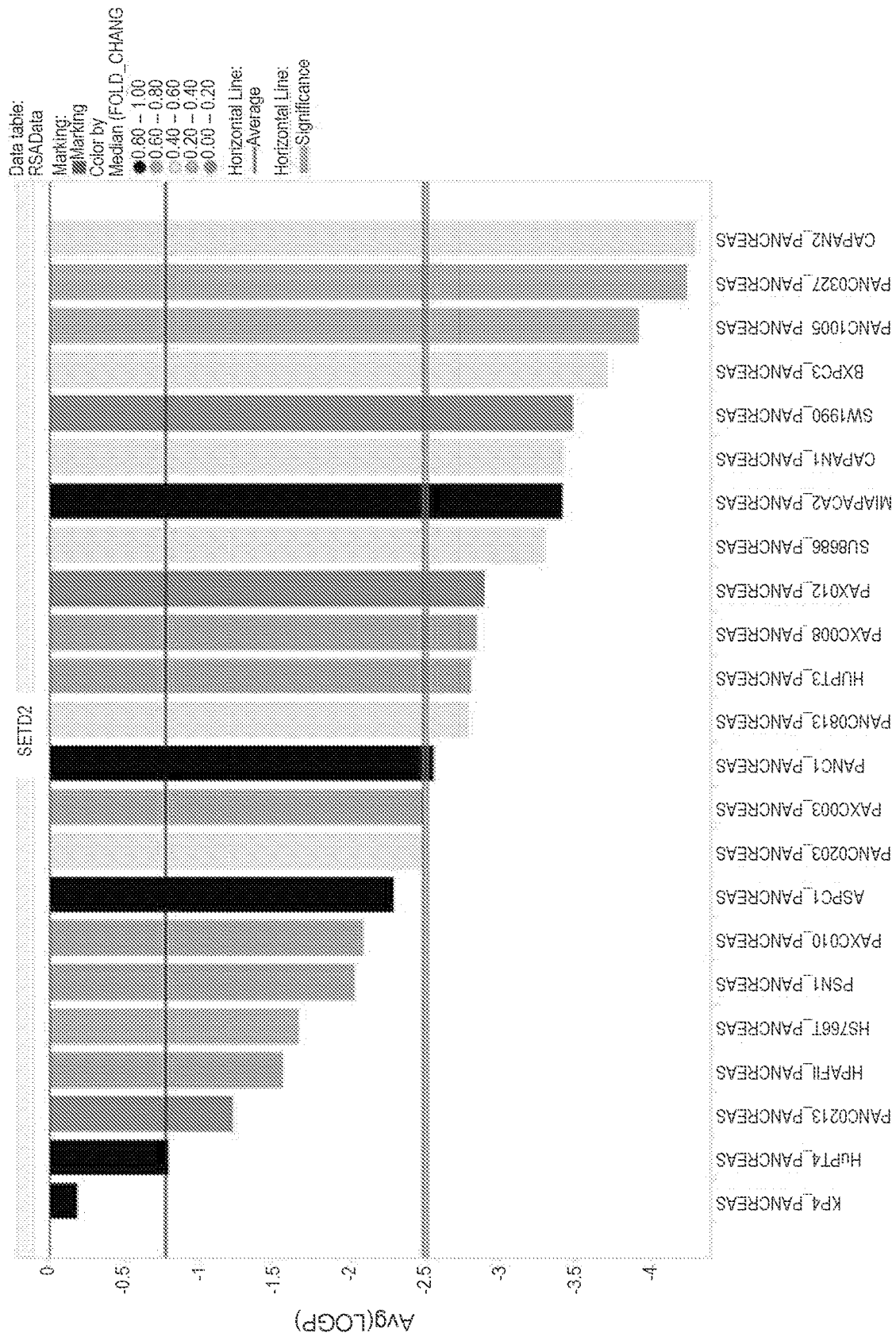

Pancreatic Ductal Adenocarcinoma (PDAC) Cell Lines are Dependent on SETD2 for Proliferation CRISPR Pooled Screening. 249 cancer cell lines and the nontransformed MCF10A cell line (control) were infected with pooled lentivirus containing a library of CRISPR-sgRNAs targeting different genes, including human SETD2. Cell lines were obtained from the ATCC, DSMZ, or JCRB cell banks. Each bar on the graphs in FIGS. 1A and 1B represents a cell line. The LogP score on the Y-axis of the graph represents the depletion of a particular target from the population. The LogP score therefore indicates the dependence of each cell line on a particular gene. In this case, each cell line with a LogP score below −2.5 was dependent on SETD2 for survival. All cell lines and their average LogP and median fold change values are presented in Table 1.

FIG. 1A shows the plot for all 250 cell lines studied. FIG. 1B shows the plot for the cell lines originating from pancreatic ductal adenocarcinoma (PDAC). Notably, FIG. 1B shows that several pancreatic cancer cell lines were significantly sensitive to depletion of the SETD2 gene.

In addition to demonstrating that cell lines derived from pancreatic cancer were sensitive to SETD2 depletion, FIG. 1A shows that additional cancer cell lines showing sensitivity to SETD2 depletion included breast, esophageal, kidney, lung, stomach, bladder/urinary tract, endometrium, skin, hematopoietic (DLBCL and AML), soft tissue, CNS, and ovarian cell lines.

TABLE 1

| CELL LINE | Avg (LOGP) | Median (FOLD_CHANGE) |
|---|---|---|
| NCIH661_LUNG | −0.1735 | 1.24 |
| KP4_PANCREAS | −0.178 | 1.45 |
| CALU3_LUNG | −0.216 | 1.03 |
| OAW42_OVARY | −0.3125 | 1.15 |
| A704_KIDNEY | −0.328 | 1.02 |
| KYSE410_OESOPHAGUS | −0.351 | 1.19 |
| NCIH522_LUNG | −0.397 | 1.01 |
| CHP212_AUTONOMIC_GANGLIA | −0.425 | 0.97 |
| NCIH1703_LUNG | −0.4445 | 1.01 |
| BICR18_UPPER_AERODIGESTIVE_TRACT | −0.446 | 0.96 |
| RCCGS_KIDNEY | −0.4525 | 1.05 |
| VMRCRCW_KIDNEY | −0.5475 | 1.21 |
| A498_KIDNEY | −0.568833333 | 1.09 |
| NCIH460_LUNG | −0.614 | 0.91 |
| SF9427_CENTRAL_NERVOUS_SYSTEM | −0.6315 | 1 |
| RCCMF_KIDNEY | −0.6355 | 0.77 |
| LIXC004NA_LIVER | −0.636 | 0.86 |
| NCIH2347_LUNG | −0.6575 | 0.5 |
| SKNDZ_AUTONOMIC_GANGLIA | −0.6835 | 0.97 |
| JHOC5_OVARY | −0.732 | 1.06 |
| RCCFG2_KIDNEY | −0.750333333 | 0.97 |
| NCIH2030_LUNG | −0.7615 | 0.86 |
| KU1919_URINARY_TRACT | −0.7745 | 0.98 |
| HUPT4_PANCREAS | −0.785 | 0.99 |
| SW780_URINARY_TRACT | −0.7915 | 1.03 |
| LK2_LUNG | −0.804 | 1.05 |
| RKO_LARGE_INTESTINE | −0.805 | 0.91 |
| JMSU1_URINARY_TRACT | −0.8125 | 0.98 |
| TE5_OESOPHAGUS | −0.827 | 0.83 |
| SKNFI_AUTONOMIC_GANGLIA | −0.8295 | 1.27 |
| SW403_LARGE_INTESTINE | −0.8315 | 0.55 |
| NCIH2196_LUNG | −0.836 | 0.89 |
| U2OS_BONE | −0.8545 | 0.87 |
| CLS439_URINARY_TRACT | −0.88525 | 0.64 |
| RT4_URINARY_TRACT | −0.887 | 1.02 |

TABLE 1-continued

| CELL LINE | Avg (LOGP) | Median (FOLD_CHANGE) |
|---|---|---|
| 5637_URINARY_TRACT | −0.891 | 0.79 |
| SKNSH_AUTONOMIC_GANGLIA | −0.891 | 0.79 |
| SKOV3_OVARY | −0.9 | 1.01 |
| KYSE150_OESOPHAGUS | −0.912666667 | 0.8 |
| OV7_OVARY | −0.959 | 0.82 |
| RCCER_KIDNEY | −0.959 | 1.09 |
| KURAMOCHI_OVARY | −0.9725 | 0.79 |
| A2780_OVARY | −0.9855 | 0.7 |
| KYSE270_OESOPHAGUS | −0.992 | 0.91 |
| 647V_URINARY_TRACT | −1.004 | 0.89 |
| ECGI10_OESOPHAGUS | −1.0145 | 0.9 |
| SJSA1_BONE | −1.0145 | 1.05 |
| VMCUB1_URINARY_TRACT | −1.0145 | 0.89 |
| SNU349_KIDNEY | −1.024 | 1.09 |
| ACHN_KIDNEY | −1.0245 | 0.95 |
| DMS114_LUNG | −1.031 | 1.02 |
| KYSE70_OESOPHAGUS | −1.032333333 | 0.97 |
| KMBC2_URINARY_TRACT | −1.034 | 1.17 |
| EFO027_OVARY | −1.049 | 0.83 |
| RMGI_OVARY | −1.056 | 0.89 |
| SBC5_LUNG | −1.056 | 0.95 |
| EOL1_HAEMATOPOIETIC_AND_LYMPHOID_TISSUE | −1.063 | 0.93 |
| LS411N_LARGE_INTESTINE | −1.0845 | 0.77 |
| TE14_OESOPHAGUS | −1.0875 | 0.81 |
| NCIH2085_LUNG | −1.101 | 0.77 |
| P31FUJ_HEMATOPOIETIC_AND_LYMPHOID_TISSUE | −1.1065 | 0.79 |
| RERFLCAI_LUNG | −1.1215 | 0.9 |
| GP2D_LARGE_INTESTINE | −1.1285 | 0.81 |
| NCIH1993_LUNG | −1.1445 | 0.97 |
| HCC15_LUNG | −1.1625 | 0.71 |
| NCIH1299_LUNG | −1.163888889 | 0.77 |
| TE8_OESOPHAGUS | −1.1805 | 0.84 |
| COV434_OVARY | −1.187 | 0.85 |
| LS1034_LARGE_INTESTINE | −1.19 | 0.96 |
| HSC3_UPPER_AERODIGESTIVE_TRACT | −1.19 | 0.77 |
| TE6_OESOPHAGUS | −1.206 | 0.84 |
| SNU1272_KIDNEY | −1.2085 | 0.41 |
| PANC0213_PANCREAS | −1.2185 | 0.17 |
| QGP1_PANCREAS | −1.23 | 0.61 |
| SW1271_LUNG | −1.23 | 0.66 |
| CAKI2_KIDNEY | −1.2305 | 0.88 |
| LS180_LARGE_INTESTINE | −1.248 | 0.71 |
| OCI-AML5_HEMATOPOIETIC_AND_LYMPHOID_TISSUE | −1.279 | 0.78 |
| NCIH2172_LUNG | −1.2835 | 0.65 |
| HCC1187_BREAST | −1.3055 | 0.74 |
| T47D_BREAST | −1.318 | 0.79 |
| NCIH1734_LUNG | −1.321 | 0.32 |
| NOMO1_HEMATOPOIETIC_AND_LYMPHOID_TISSUE | −1.3215 | 0.49 |
| CAL54_KIDNEY | −1.326 | 0.84 |
| DLD1_LARGE_INTESTINE | −1.35 | 0.96 |
| UMUC3_URINARY_TRACT | −1.359 | 0.89 |
| KNS42_CENTRAL_NERVOUS_SYSTEM | −1.367 | 0.64 |
| TUHR4TKB_KIDNEY | −1.3755 | 0.82 |
| A427_LUNG | −1.4055 | 0.68 |
| NCIH1975_LUNG | −1.408 | 0.69 |
| IALM_LUNG | −1.4165 | 0.67 |
| DV90_LUNG | −1.4285 | 0.8 |
| A549_LUNG | −1.431285714 | 0.7 |
| KMRC2_KIDNEY | −1.439 | 0.77 |
| SCC25_UPPER_AERODIGESTIVE_TRACT | −1.4405 | 0.44 |
| TYKNU_OVARY | −1.447 | 0.9 |
| NCIH2066_LUNG | −1.4545 | 0.81 |
| NCIH1563_LUNG | −1.46 | 0.57 |
| NCIH1944_LUNG | −1.462 | 0.62 |
| RCCWK_KIDNEY | −1.4705 | 0.79 |
| NCIH1793_LUNG | −1.471 | 0.76 |
| J82_URINARY_TRACT | −1.4795 | 0.83 |
| NCIH1693_LUNG | −1.4845 | 0.84 |
| CAOV3_OVARY | −1.493 | 0.62 |
| OE19_OESOPHAGUS | −1.5155 | 0.96 |
| BFTC909_KIDNEY | −1.522 | 0.79 |
| SW900_LUNG | −1.5305 | 0.7 |
| RT112_URINARY_TRACT | −1.5405 | 0.85 |
| KYSE510_OESOPHAGUS | −1.5415 | 0.86 |
| HPAFII_PANCREAS | −1.549 | 0.62 |
| BT549_BREAST | −1.5525 | 0.55 |
| MCF10A_BREAST_NONTRANSFORMED | −1.567 | 0.51 |

TABLE 1-continued

| CELL LINE | Avg (LOGP) | Median (FOLD_CHANGE) |
|---|---|---|
| HT1376_URINARY_TRACT | −1.571 | 0.77 |
| SNGM_ENDOMETRIUM | −1.5735 | 0.81 |
| OVISE_OVARY | −1.574 | 0.48 |
| SAOS2_BONE | −1.592 | 0.72 |
| NCIH1573_LUNG | −1.5945 | 0.69 |
| NCIH441_LUNG | −1.606 | 0.53 |
| NCIH2122_LUNG | −1.6135 | 0.76 |
| COLO680N_OESOPHAGUS | −1.6205 | 0.62 |
| T84_LARGE_INTESTINE | −1.625 | 0.71 |
| DMS53_LUNG | −1.6325 | 0.79 |
| T24_URINARY_TRACT | −1.635 | 0.74 |
| TCCSUP_URINARY_TRACT | −1.635666667 | 0.67 |
| MDAMB134VI_BREAST | −1.6395 | 0.93 |
| HS766T_PANCREAS | −1.654 | 0.39 |
| TUHR14TKB_KIDNEY | −1.7 | 0.73 |
| MDAMB453_BREAST | −1.7065 | 0.7 |
| 639V_URINARY_TRACT | −1.707 | 0.65 |
| YD8_UPPER_AERODIGESTIVE_TRACT | −1.724 | 0.49 |
| TUHR10TKB_KIDNEY | −1.7265 | 0.55 |
| NB1_AUTONOMIC_GANGLIA | −1.773333333 | 0.89 |
| HCT116_LARGE_INTESTINE | −1.791 | 0.8 |
| OCI-AML2_HEMATOPOIETIC_AND_LYMPHOID_TISSUE | −1.804 | 0.77 |
| BC3C_URINARY_TRACT | −1.805 | 0.76 |
| BT20_BREAST | −1.8375 | 0.75 |
| RCCJW_KIDNEY | −1.8425 | 0.67 |
| HSC2_UPPER_AERODIGESTIVE_TRACT | −1.851 | 0.74 |
| ECA109_OESOPHAGUS | −1.868 | 0.57 |
| HS578T_BREAST | −1.868 | 0.47 |
| CALU6_LUNG | −1.886 | 0.87 |
| TT_OESOPHAGUS | −1.8865 | 0.75 |
| NCIH2023_LUNG | −1.8945 | 0.55 |
| SCABER_URINARY_TRACT | −1.902 | 0.79 |
| HEC1A_ENDOMETRIUM | −1.902 | 0.66 |
| TE15_OESOPHAGUS | −1.903 | 0.67 |
| KMRC20_KIDNEY | −1.9115 | 0.81 |
| SW1710_URINARY_TRACT | −1.9165 | 0.86 |
| OSRC2_KIDNEY | −1.9175 | 0.74 |
| KYSE180_OESOPHAGUS | −1.9365 | 0.85 |
| HEC151_ENDOMETRIUM | −1.952 | 0.6 |
| HCC1428_BREAST | −1.953 | 0.68 |
| 786O_KIDNEY | −1.957666667 | 0.6 |
| HEC1B_ENDOMETRIUM | −1.9855 | 0.53 |
| NCIH520_LUNG | −1.991 | 0.75 |
| NCIH1048_LUNG | −2.0155 | 0.71 |
| PSN1_PANCREAS | −2.026 | 0.75 |
| SKNBE2_AUTONOMIC_GANGLIA | −2.027 | 0.82 |
| C2BBE1_LARGE_INTESTINE | −2.032 | 0.68 |
| NCIH1792_LUNG | −2.0345 | 0.66 |
| NCIH838_LUNG | −2.0475 | 0.5 |
| NCIH2126_LUNG | −2.048 | 0.53 |
| NCIH226_LUNG | −2.066 | 0.46 |
| PAXC010_PANCREAS | −2.079 | 0.64 |
| HOS_BONE | −2.09 | 0.79 |
| RC124_KIDNEY | −2.1005 | 0.61 |
| SKNAS_AUTONOMIC_GANGLIA | −2.1005 | 0.5 |
| HSC4_UPPER_AERODIGESTIVE_TRACT | −2.123 | 0.51 |
| SKBR3_BREAST | −2.1235 | 0.63 |
| SNU423_LIVER | −2.1285 | 0.69 |
| HCT15_LARGE_INTESTINE | −2.139 | 0.86 |
| CAL29_URINARY_TRACT | −2.15 | 0.51 |
| P31FUJ_HAEMATOPOIETIC_AND_LYMPHOID_TISSUE | −2.166 | 0.55 |
| TE1_OESOPHAGUS | −2.1685 | 0.7 |
| HBCLS2_URINARY_TRACT | −2.172 | 0.53 |
| OCIM2_HAEMATOPOIETIC_AND_LYMPHOID_TISSUE | −2.1835 | 0.79 |
| NCIH358_LUNG | −2.184 | 0.6 |
| NCIH23_LUNG | −2.2455 | 0.48 |
| HT1197_URINARY_TRACT | −2.275 | 0.45 |
| ASPC1_PANCREAS | −2.2835 | 0.81 |
| KYSE140_OESOPHAGUS | −2.369 | 0.61 |
| MDAMB157_BREAST | −2.396 | 0.21 |
| HPAC_PANCREAS | −2.398 | 0.72 |
| HCC1143_BREAST | −2.414 | 0.39 |
| NCIH2110_LUNG | −2.4255 | 0.76 |
| THP1_HEMATOPOIETIC_AND_LYMPHOID_TISSUE | −2.4375 | 0.81 |
| KARPAS422_HAEMATOPOIETIC_AND_LYMPHOID_TISSUE | −2.4535 | 0.54 |
| BFTC905_URINARY_TRACT | −2.4675 | 0.68 |
| PANC0203_PANCREAS | −2.478 | 0.56 |

TABLE 1-continued

| CELL LINE | Avg (LOGP) | Median (FOLD_CHANGE) |
|---|---|---|
| PAXC003_PANCREAS | −2.4795 | 0.63 |
| YD10B_UPPER_AERODIGESTIVE_TRACT | −2.5015 | 0.62 |
| CAKI1_KIDNEY | −2.5105 | 0.49 |
| SUM149PT_BREAST | −2.5225 | 0.43 |
| GI1_CENTRAL_NERVOUS_SYSTEM | −2.523 | 0.49 |
| PANC0504_PANCREATIC | −2.5245 | 0.6 |
| PANC1_PANCREAS | −2.548 | 0.8 |
| SCC4_UPPER_AERODIGESTIVE_TRACT | −2.5855 | 0.47 |
| PANC0403_PANCREAS | −2.6325 | 0.38 |
| MDAMB468_BREAST | −2.66 | 0.58 |
| OCIM1_HAEMATOPOIETIC_AND_LYMPHOID_TISSUE | −2.667 | 0.5 |
| NUGC3_STOMACH | −2.6765 | 0.6 |
| VMRCRCZ_KIDNEY | −2.7035 | 0.67 |
| HCC1937_BREAST | −2.7325 | 0.42 |
| MFE280_ENDOMETRIUM | −2.745 | 0.5 |
| HS729_SOFT_TISSUE | −2.757 | 0.67 |
| MG63_BONE | −2.784 | 0.7 |
| PANC0813_PANCREAS | −2.784 | 0.49 |
| HBCLS1_URINARY_TRACT | −2.789333333 | 0.56 |
| HUPT3_PANCREAS | −2.806 | 0.62 |
| MDAMB361_BREAST | −2.827 | 0.72 |
| PAXC008_PANCREAS | −2.8395 | 0.63 |
| TE10_OESOPHAGUS | −2.8645 | 0.7 |
| OE33_OESOPHAGUS | −2.8795 | 0.54 |
| PAX012_PANCREAS | −2.8885 | 0.09 |
| NCIH727_LUNG | −2.89 | 0.55 |
| A375_SKIN | −2.921666667 | 0.49 |
| RT11284_URINARY_TRACT | −2.9565 | 0.77 |
| SKM1_HEMATOPOIETIC_AND_LYMPHOID_TISSUE | −2.98 | 0.74 |
| FARAGE_HAEMATOPOIETIC_AND_LYMPHOID_TISSUE | −3.016 | 0.62 |
| MDAMB231_BREAST | −3.1095 | 0.51 |
| NCIH810_LUNG | −3.1445 | 0.66 |
| TE11_OESOPHAGUS | −3.192 | 0.7 |
| OV90_OVARY | −3.252 | 0.65 |
| SU8686_PANCREAS | −3.296 | 0.53 |
| LS123_LARGE_INTESTINE | −3.345 | 0.33 |
| OCI-AML3_HEMATOPOIETIC_AND_LYMPHOID_TISSUE | −3.3725 | 0.74 |
| HCC827_LUNG | −3.411 | 0.54 |
| CAPAN1_PANCREAS | −3.4135 | 0.42 |
| KP2_PANCREAS | −3.4225 | 0.55 |
| SW1990_PANCREAS | −3.4765 | 0.06 |
| MIAPACA2_PANCREAS | −3.51475 | 0.72 |
| YD38_UPPER_AERODIGESTIVE_TRACT | −3.588 | 0.46 |
| MDAMB436_BREAST | −3.621 | 0.49 |
| BXPC3_PANCREAS | −3.7085 | 0.46 |
| UBLC1_URINARY_TRACT | −3.724 | 0.64 |
| OVMANA_OVARY | −3.736 | 0.64 |
| 769P_KIDNEY | −3.762714286 | 0.49 |
| NCIH322_LUNG | −3.8915 | 0.49 |
| PANC1005_PANCREAS | −3.917 | 0.37 |
| TE4_OESOPHAGUS | −3.948666667 | 0.34 |
| HCC1806_BREAST | −4.0125 | 0.36 |
| MDAMB415_BREAST | −4.1585 | 0.37 |
| NCIH647_LUNG | −4.1735 | 0.43 |
| KYSE30_OESOPHAGUS | −4.227 | 0.32 |
| PANC0327_PANCREAS | −4.233 | 0.39 |
| CAPAN2_PANCREAS | −4.2915 | 0.5 |
| TE9_OESOPHAGUS | −4.457 | 0.42 |
| HCC38_BREAST | −5.106 | 0.32 |
| OE21_OESOPHAGUS | −5.314 | 0.49 |
| MOLM13_HEMATOPOIETIC_AND_LYMPHOID_TISSUE | −7.1595 | 0.31 |

Validation of the CRISPR pooled screen. SU8686 is a cell line derived from Pancreatic Ductal Adenocarcinoma. Cell lines were infected with CRISPR viruses containing dual sgRNAs targeting two sites of SETD2. Proliferation of the cell lines was measured by automated cell counting over time. As shown in FIG. 2B, combinations of sgRNAs where one or both of the two sgRNAs targeting the active site of SETD2 were included, were found to have a dramatic effect on the proliferation of this pancreatic cancer cell line. In contrast, sgRNAs that targeted a negative control, SMARCA2, had no effect on proliferation.

Figure 2A:
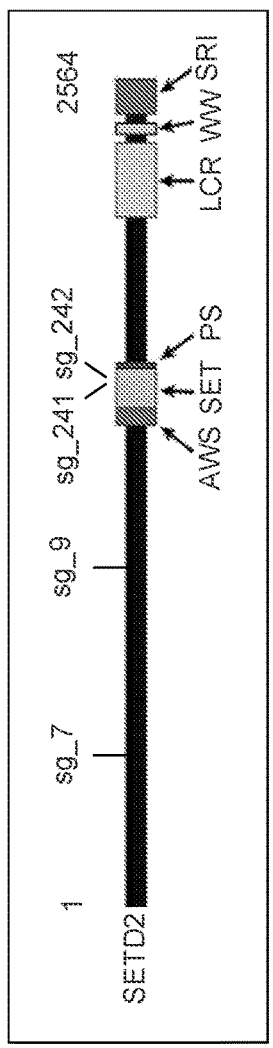
Figure 2B:
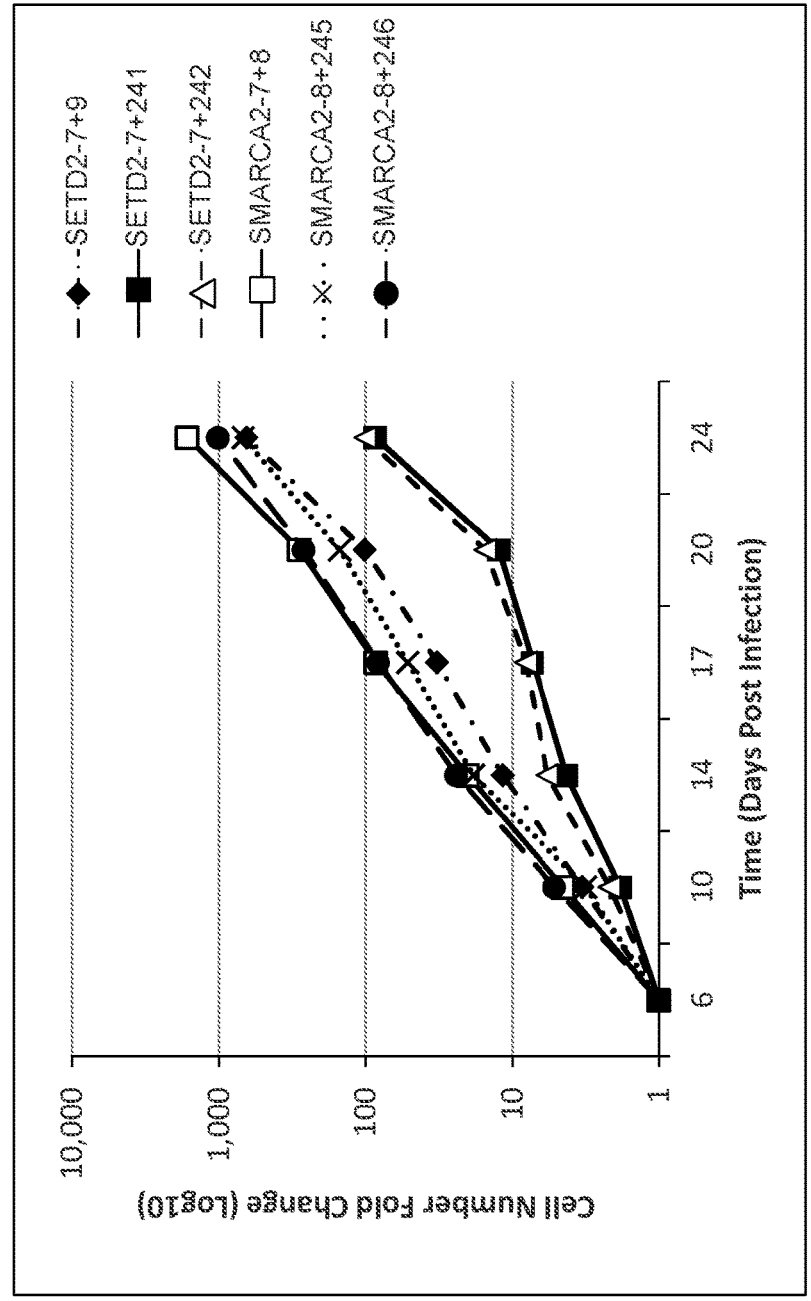

The proliferation data in FIG. 2B was then confirmed using next generation sequencing (NGS) of sgRNA cut sites, shown in FIGS. 2C and 2D. The bar charts in FIGS. 2C and 2D show the genotypes of cells that survived infection over time. Bars filled in show the percentage of wild-type (uncut) alleles; bars in white show in-frame insertions and deletions (possibly non-inactivating); and bars filled in show out-of-frame insertions and deletions (non-activating). As shown in FIG. 2C, in SETD2 sgRNA infecting cells, the wild-type (uncut) population of alleles increases over time, indicating that cells with functional SETD2 have a survival advantage over cells with non-functional SETD2. In contrast, FIG. 2D shows that the genotype associated with SMARCA2 sgRNAs remain constant over time, indicating that SMARCA2 activity is not required for SU8686 viability and growth.

In conclusion, FIGS. 2B-D show that the PDAC cell line, SU8686, is dependent on SETD2 for proliferation, based on a dual sgRNA assay.

Figure 3A:
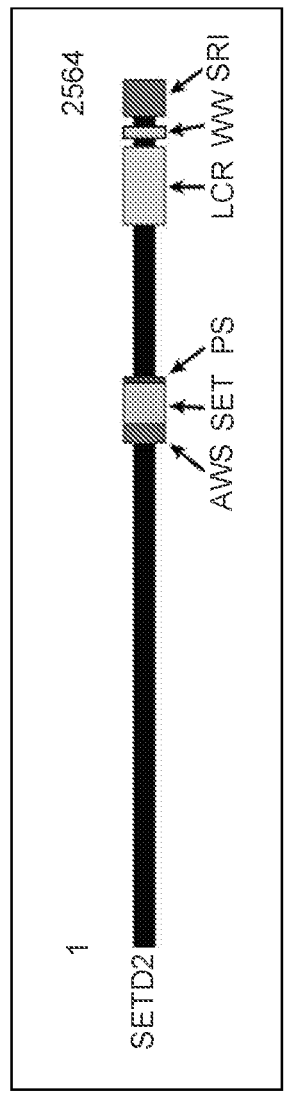
FIGS. 3A-3B demonstrate that CRISPR domain pool screening of the OE21 esophageal cancer cell line identifies the SET domain as important for SETD2 sensitivity.
Figure 3B:
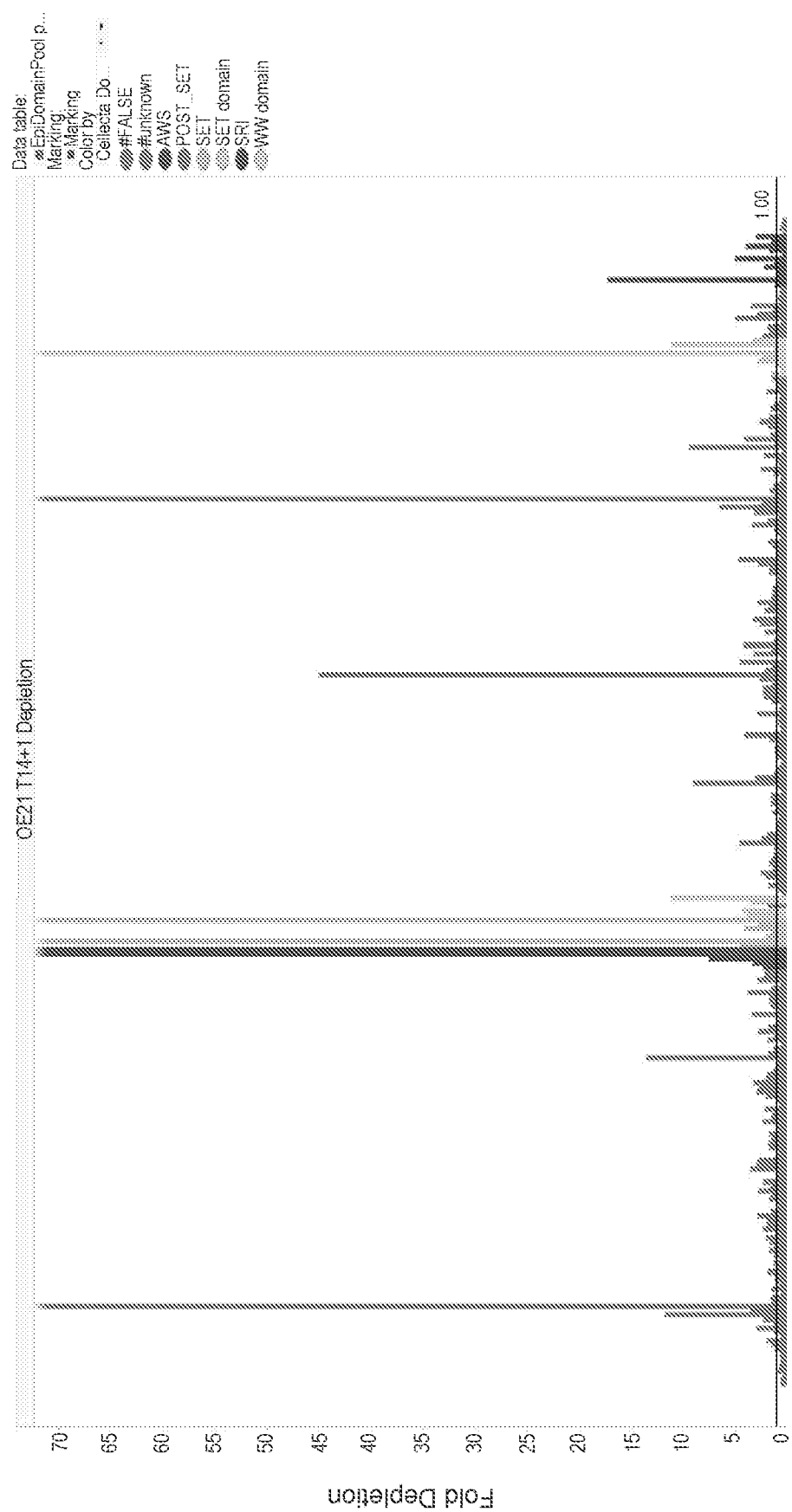

CRISPR domain pool screening identifies the SET domain. This screen utilized sgRNAs targeting the entire length of the SETD2 gene (depicted in FIG. 3A). Domains that are important for the function of the encoded protein are depleted at a higher rate than other regions of the protein. This is due to the fact that functional domains have a much lower tolerance for mutations than other regions. As shown in FIG. 3B, CRISPR domain screening of the OE21 esophageal cell line shows a very strong depletion signal from the SET domain and the "associated with SET" (AWS) domain of SETD2 (shown in FIG. 3A), indicating that targeting the SET domain/active site of SETD2, e.g., with a small molecule inhibitor, will result in a growth phenotype (i.e., reduced proliferation) in this cell line.

Summary of Dual Assay Target Validation. A summary of target validation studies is provided in the Table of FIG. 4. CRISPR pooled screening results for selected cell lines are shown in the "Epipool column." Domain specific CRISPR pooled screening results are shown in the "Epidomain pool column." These results indicate that the SET domain of SETD2 is required for the effect. The validation of CRISPR pooled screening results in cell lines by dual sgRNA CRISPR assay (FIG. 2B) and NGS confirmation (as shown in FIG. 2C and FIG. 2D) are shown in the "Proliferation" and "NGS" columns in FIG. 4. Boxes marked as are sensitive boxes in grey are insensitive; boxes marked as indicate inconclusive results; boxes in white indicate that data are not available.

Conclusion: Based on a dual signal RNA (sgRNA) assay, the pancreatic cancer cell line, SU8686, as well as several other cancer-derived cell lines, such as, e.g., those derived from breast, ovary, lung, stomach, kidney, esophagus, bladder, CNS, soft tissue, and skin, are dependent on SETD2 activity for their viability and growth, and the SET domain in particular. Thus, inhibiting the histone methyltransferase SETD2 (i.e., with small molecule inhibitors such as alkyl-sinefungins) has broad implications in the treatment of numerous cancers, and especially, pancreatic cancer.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All patents and publications mentioned in the specification are indicative of the levels of those of ordinary skill in the art to which the disclosure pertains. All patents and publications are herein incorporated by reference to the same extent as if each individual publication was specifically and individually indicated to be incorporated by reference.

The invention claimed is:

1. A method of reducing or inhibiting proliferation of a cancer cell, comprising (i) contacting a cancer cell with an effective amount of a Suppressor of variegation, Enhancer of zeste, and Trithorax domain containing 2 (SETD2) inhibitor, wherein the SETD2 inhibitor is N-propyl sinefungin or N-benzyl sinefungin; and (ii) reducing or inhibiting proliferation of said cancer cell, wherein said cancer cell is a pancreatic ductal carcinoma cell line or an esophageal cancer cell line OE21.

* * * * *

SEQUENCE LISTING

<160> NUMBER OF SEQ ID NOS: 6

<210> SEQ ID NO 1
<211> LENGTH: 19
<212> TYPE: RNA
<213> ORGANISM: Homo sapiens

<400> SEQUENCE: 1
uaaaggaggu auaucgaau                                                  19

<210> SEQ ID NO 2
<211> LENGTH: 19
<212> TYPE: RNA
<213> ORGANISM: Homo sapiens

<400> SEQUENCE: 2
gagagguacu cgaucauaa                                                  19

<210> SEQ ID NO 3
<211> LENGTH: 19
<212> TYPE: RNA
<213> ORGANISM: Homo sapiens

<400> SEQUENCE: 3
gcucagaguu aacguuuga                                                  19

```
<210> SEQ ID NO 4
<211> LENGTH: 19
<212> TYPE: RNA
<213> ORGANISM: Homo sapiens

<400> SEQUENCE: 4
ccaaagauuc agacauaua                                                   19

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
agcaccagta acagagccag                                                  20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
gactgtgaac ggacaactga                                                  20
```